United States Patent [19]

Jacquet et al.

[11] Patent Number: 4,517,174

[45] Date of Patent: May 14, 1985

[54] HAIR TREATMENT COMPOSITIONS BASED ON POLYCATIONIC POLYMERS

[75] Inventors: Bernard Jacquet, Antony; Gérard Lang, Epinay-sur-Seine; Alain Malaval, Aulnay-sous-Bois; Serge Forestier, Claye Souilly; Do Le Trung, Drancy, all of France

[73] Assignee: Societe Anonyme dite: L'Oreal, Paris, France

[21] Appl. No.: 534,366

[22] Filed: Sep. 21, 1983

Related U.S. Application Data

[62] Division of Ser. No. 217,411, Dec. 17, 1980, Pat. No. 4,411,884.

[30] Foreign Application Priority Data

Dec. 21, 1979 [FR] France ............................... 79 31431

[51] Int. Cl.$^3$ .................... A61K 7/06; A61K 7/135
[52] U.S. Cl. ................................... 424/62; 424/70; 8/405
[58] Field of Search .............. 8/414, 415, 416, 421, 8/423, 405; 424/70, 71, 72, 62

[56] References Cited

U.S. PATENT DOCUMENTS

| | | | |
|---|---|---|---|
| 4,119,399 | 10/1978 | Feinland et al. | 8/423 |
| 4,157,388 | 6/1979 | Christiansen | 424/71 |
| 4,240,450 | 12/1980 | Grollier et al. | |
| 4,348,202 | 9/1982 | Grollier et al. | 424/70 |
| 4,381,919 | 5/1983 | Jacquet et al. | 8/405 |
| 4,402,700 | 9/1983 | Feinland et al. | 8/416 |
| 4,411,884 | 10/1983 | Jacquet et al. | |

FOREIGN PATENT DOCUMENTS 2000164  1/1979  United Kingdom .

*Primary Examiner*—Delbert R. Phillips
*Assistant Examiner*—F. T. Moezie
*Attorney, Agent, or Firm*—Cushman, Darby and Cushman

[57] ABSTRACT

A hair dye or hair bleaching composition contains in an aqueous carrier a quaternized polymer.

13 Claims, No Drawings

HAIR TREATMENT COMPOSITIONS BASED ON POLYCATIONIC POLYMERS

This is a division of application Ser. No. 217,411, filed Dec. 17, 1980, now U.S. Pat. No. 4,411,884.

This invention has as its object the use of cationic polymers as cosmetic agents, cosmetic compositions containing these polymers, and a process of treating hair, skin or nails with said polymers.

It has already been proposed to use various cationic polymers as pesticides, flocculating agents, etc. It has also been proposed to use certain cationic polymers as cosmetic agents; see, for example, French Pat. No. 75.15162.

It has now been discovered that the use of certain particular cationic polymers offers advantages in comparison with cationic polymers previously used. Some of these advantages will be disclosed below in the present specification.

The invention has for its object the use as cosmetic agents polymers containing groups of the formula (I):

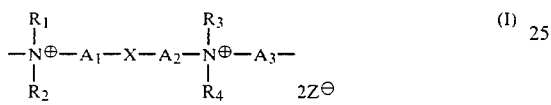

wherein:

$R_1$, $R_2$, $R_3$, $R_4$ independently represent a hydrocarbon group, possibly substituted, or else the couples $R_1$, $R_2$ and/or $R_3$, $R_4$ represent, with the nitrogen atom with which they are bonded, a heterocycle that can contain in addition an oxygen or sulfur heteroatom;

$A_1$ and $A_2$, identical or different, represent linear or branched alkylene groups or arylene, which are substituted or not, able to contain up to 20 carbon atoms;

X represents a bivalent group of the formula:

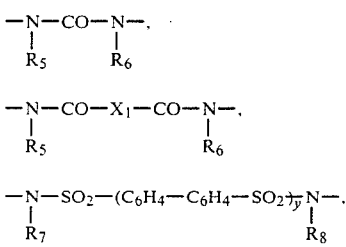

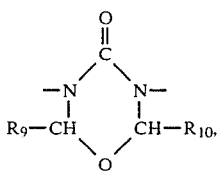

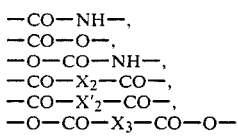

wherein:
y is equal to 0 or 1,
$R_5$, $R_6$, $R_7$, $R_8$, $R_9$ and $R_{10}$ represent a hydrogen atom or represent a lower alkyl group, $X_1$ represents an alkylene group, an alkylene group comprising a heteroatomic —S—S— group, an alkenylene, arylene, diaminoalkylene, diaminoarylene, dioxyalkylene, dioxyarylene, polyoxyalkylene group or else $X_1$ represents a direct covalent bond, $X_2$ represents a diaminoalkylene, dioxyalkylene or polyoxyalkylene bivalent group, $X'_2$ is a dithioalkylene group, $X_3$ is an alkylene, cycloalkylene, or arylene group, substituted or not, or else $X_3$ represents a diaminoalkylene, diaminocycloalkylene or diaminoarylene group.

$A_3$ represents a bivalent group of the formula:

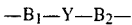

wherein:

$B_1$ and $B_2$ are alkylene or arylene groups, and Y has the same definition as X, or Y represents the group:

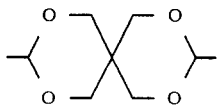

or else $A_3$ represents a linear or branched alkylene group substituted or not by one or more =O groups, and/or interrupted by one or more heteroatoms and heteroatom groups of oxygen, sulfur or nitrogen, and/or by one or several arylene groups, or else $A_3$ represents a group of the formula —$B_3$—$Y_1$—$B_4$— wherein $B_3$ and $B_4$ represent arylene groups and $Y_1$ represents a linear or branched alkylene group, possibly substituted by one or more —OH or =O groups, or $Y_1$ represents a heteroatom or a group of heteroatoms of oxygen, sulfur or nitrogen, or else $A_3$ represents a group:

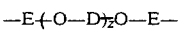

or

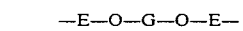

z being a number that can vary from 2 to 600,

E representing an alkylene group having 1 to 4 carbon atoms, a —$CH_2$—CHOH—$CH_2$— group, D representing a bivalent hydrocarbon containing from 1 to 5 carbon atoms, and G being a hydrocarbon group such as an alkylene, cycloalkylene, arylene or aralkylene possibly substituted or else when X is different from —CO—$X_2$—CO—, $A_3$ can represent a linear or branched alkylene or hydroxyalkylene group, able to comprise double bonds, or a cycoalkylene group that can comprise double bonds that can contain up to 20 carbon atoms;

and $Z^\ominus$ represents an anion;

it being understood that when X represents a group

$A_3$ then represents a group of the formula

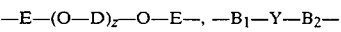

(Y then being able to have the same value as X given above except the value —NH—CO—NH—), or —E—O—G—O—E—

(E and G then not being able simultaneously to represent an alkylene).

For simplification, the polymers whose recurrent groups answer to formula (I) will be designated by the expression "formula I polymers."

The end groups of the formula (I) polymers vary with the starting reagents and their proportions. They can particularly be of the

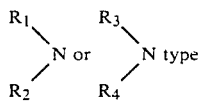

or of the Z—A$_3$—, Z—A, or Z—A$_2$ type.

Of the formula (I) polymers, there will be mentioned those for which X represents —NH—CO—NH; those for which X represents —N(R$_5$)—CO—N(R$_6$)— and A$_3$ then represents a group —E—(O—D)$_z$—O—E,

—B$_1$—Y—B$_2$—

(Y then having the same values as X except the value —NH—CO—NH), or —E—O—G—O—E—

(E and G then not being able simultaneously to represent an alkylene); and those for which X is different from —N(R$_5$)—CO—N(R$_6$)—.

In the formula (I) polymers, $Z^\ominus$ represents a nontoxic anion compatible with a cosmetic use, derived from an inorganic acid, particularly a halide (bromide, iodide or chloride) anion or an anion derived from other inorganic acids, for example, a sulfate anion, etc. or again an anion derived from an organic (of slight molecular weight) sulfonic or carboxylic acid, particularly an alkanoic acid having 2 to 12 carbon atoms (for example, acetic acid), benzoic acid, lactic acid, citric acid, or paratoluene-sulfonic acid; the substitutents R$_1$, R$_2$, R$_3$ and R$_4$ represent particularly an aryl group, an aliphatic (in particular alkyl or alkenyl) substituted or not, alicyclic (in particular cycloalkyl) or arylaliphatic group containing at most 20 carbon atoms; for example R$_1$, R$_2$, R$_3$ and R$_4$ represent an alkyl or hydroxyalkyl group having 1 to 8 carbon atoms, a cycloalkyl-alkyl group having less than 20 carbon atoms and preferably not having more than 16 carbon atoms, a cycloalkyl group with 5 or 6 groups, an aralkyl group such as a phenylalkyl group whose alkyl group preferably comprises 1 to 3 carbon atoms; when the two residues R$_1$ and R$_2$ or R$_3$ and R$_4$, attached to the same nitrogen atom, with it constitute a ring, they can together represent preferably a polymethylene radical having 2 to 6 carbon atoms, and the ring can further comprise an oxygen or sulfur heteroatom;

A$_1$, A$_2$, B$_1$, B$_2$ particularly represent a linear or branched alkylene group having 1 to 12 carbon atoms in the chain, and possibly comprising one or more (in particular from 1 to 4) alkyl substitutents in the branching, said branching substituents having in particular 1 to 10, and especially 1 to 4, carbon atoms; X$_1$ can particularly represent an alkylene group (defined as above for A$_1$, A$_2$, B$_1$, B$_2$), said alkylene group being able to be interrupted by the —S—S— group, or being able to comprise in addition at each end an —NH— group, or an —O— group; or else X$_1$ can represent an alkenylene group having 4 to 20 carbon atoms; or X$_1$ can represent a polyoxyalkylene group of the formula —D$_1$—(OD$_1$)$_{z_1}$— wherein D$_1$ represents an alkylene group having 1 to 5 carbon atoms and z$_1$ is a number varying from 1 to 40; or X$_1$ represents an arylene group having 6 to 20 carbon atoms such as a group —C$_6$H$_4$— or —C$_6$H$_4$—C$_6$H$_4$—, said arylene group being able to be substituted by one or more alkyl groups (particularly having 1 to 3 carbon atoms), and particularly by a methyl or ethyl group, and said arylene group being able to comprise an —NH— or —O— group at each end;

X$_2$ represents an —NH—alkylene—NH— or —O—alkylene—O— group, the alkylene being defined as above for A$_1$, for example:

or else X$_2$ represents a group

—D$_1$—(OD$_1$)$_{z_1}$—

D$_1$ and z$_1$ being defined as above.

X'$_2$ represents a dithioalkylene group whose alkylene is defined as above, for example, for A$_1$;

X$_3$ is an alkylene group (defined as for A$_1$), or an arylene group having 6 to 20 carbon atoms (defined and being able to be substituted as for X$_1$), or a cycloalkylene group having 5 to 20 carbon atoms, said alkylene group having 5 to 20 carbon atoms, said groups being able further to comprise an —NH— group at each end;

A$_3$ can represent an alkylene group (as defined for example for A$_1$), possibly substituted by one or more —OH— or =O groups (A$_3$, for example, representing —CH$_2$—CO—CH$_2$—), and/or interrupted by one or more heteroatomoic groups such as —O—, —S—, —SO—, —SO$_2$—, —S—S—, or

R$_{11}$ in particular being an alkyl (preferably 1 to 10 C.), an aryl (preferably 6 to 20 C.), a cycloalkyl (preferably 5 to 20 C.), or an aralkyl (preferably 7 to 20 C.), and/or interrupted by one or more arylene groups, A$_3$, for example, representing

—CH$_2$—C$_6$H$_4$—CH$_2$—,

—CH$_2$—(C$_6$H$_4$)$_2$—CH$_2$—,

—CH$_2$C$_6$H$_4$—O—C$_6$H$_4$CH$_2$—, or —CH$_2$—O—G—O—CH$_2$—,

G being defined as above;

When A$_3$ represents the group —B$_3$—Y$_1$—B$_4$—, B$_3$ and B$_4$ are particularly arylene groups having 6 to 20 carbon atoms, particularly phenylene groups, and Y$_1$ is particularly a linear or branched alkylene, possibly substituted, having 1 to 6 carbon atoms, or else Y$_1$ is a heteroatom or a heteroatomic group such as those already mentioned above, i.e.

$$-O-, -S-, -SO-, -SO_2-, -S-S-, \text{ or}$$

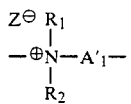

$A_3$ then representing $$-C_6H_4-SO_2-C_6H_4-,$$

$$-C_6H_4-CH_2-C_6H_4-,$$

$$-C_6H_4-C(CH_3)_2-C_6H_4-,$$

$$-C_6H_4-CO-C_6H_4-,$$

or $-C_6H_4-CHOH-C_6H_4-$;

and when $A_3$ represents $-E+OD)_{\overline{z}}OE-$

D represents a group $-(CH_2)_2-$, $-CH_2-CH(CH_3)-$ or $-(CH_2)_2-$, and z can vary particularly from 2 to 18.

It should be noted that the invention extends to the cosmetic use of formula (I) polymers wherein the groups $A_1$, X, $A_2$, $A_3$, $R_1$, $R_2$, $R_3$ and/or $R_4$ have several different values in the same polymer I.

In addition, the formula I polymers can be copolymers further containing formula I' groups:

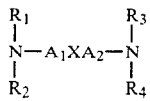

wherein $A'_1$ is a saturated or unsaturated linear or branched hydrocarbon, particularly a substituted or unsubstituted alkylene or arylene group having up to 20 carbon atoms.

The formula (I) polymers can be prepared by a standard process consisting in submitting to a polycondensation reaction a ditertiary diamine of the formula:

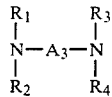

wherein:

$A_1$, X, $A_2$, $R_1$, $R_2$, $R_3$ and $R_4$ are defined above, with a compound of the formula $Z-A_3-A$, Z and $A_3$ being defined as above.

Formula (I) polymers can also be prepared by causing a ditertiary diamine of the formula

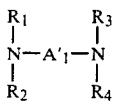

to react on a derivative of the formula $$Z-Z_1XA_2-Z.$$

Further, to obtain copolymers containing formula I' groups, a part of the ditertiary diamine mentioned above is replaced by a tertiary diamine of the type $$\begin{array}{cc} R_1 & R_3 \\ | & | \\ N-A'_1-N \\ | & | \\ R_2 & R_4 \end{array}$$

or a part of the compound $Z-A_3-Z$ or $Z-A_1X-A_2-Z$, for example, by the compound $Z-A'_1-Z-$.

The polycondensation reaction is performed, for example, in a solvent or mixture of solvents favoring quaternization reactions, such as water, dimethylformamide, acetonitrile, lower alcohols, particularly lower alkanols such as methanols, etc.

The reaction temperature can vary between 10° and 150° C. and preferably between 20° and 100° C.

The reaction time depends on the nature of the solvent, starting reagents and degree of polymerization desired.

Generally, the starting reagents are made to react in equimolecular amounts, but it is possible to use either diamine or dihalide in slight excess, this excess being less than 20% in moles.

The resulting polycondensate is optionally isolated at the end of the reaction either by filtration or by concentration of the reaction mixture.

It is possible to regulate the average length of the chains by adding, at the beginning or during the reaction, a slight amount (1 to 15% in moles in relation to one of the reagents) of a monofunctional reagent such as a tertiary amine or a monohalide. In this case, at least a part of the end groups of the resulting polymer I consists of either the tertiary amine groups used or the hydrocarbon group of the monohalide.

Some formula (I) polymers are known particularly from French Pat. No. 78.17373 and from British Pat. No. 1,288,006.

The invention extends to the cosmetic use of formula (I) polymers having such end groups.

Instead of the starting reagent it is also possible to use either a mixture of ditertiary diamines or a mixture of dihalides or again a mixture of ditertiary amines and a mixture of dihalides provided that the ratio of the total molar amounts of diamines and dihalides is close to 1.

The starting products of formula $A_3(Z)_2$ can be prepared by standard methods like those described, for example, in French patent application No 76.02948; by Perry-Hibbert, Canad. J. Res. (B), 14 (1936), 82; Fordyce and Lowell H., J. Am. Chem. Soc., 61 (1939), 190; Johansson, Eur. J. Biochem., 33, 379 (1973).

The starting ditertiary diamines can be prepared by standard processes like those described, for example, in French Pat. No. 75.15162; U.S. Pat. No. 4,110,263.

Further, in case, for example, the starting diamine is of the type:

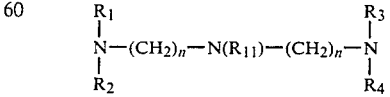

it is possible to obtain a crosslinked polymer either by using an excess of reagent $A_3(Z)_2$ or after having made said starting amine react with a fairly equimolecular amount of reagent $A_3(Z)_2$, by making the resulting polymer react with another bifunctional derivative. Thus, it is possible to obtain any variety of polymers (I) having variable degrees of crosslinking.

The invention particularly has for its object the use of formula I polymers described below in the experimental part.

Although the invention is not limited to use of polymer I with a degree of polymerization varying in a particular field, it can be pointed out that the formula (I) polymers that can be used according to the invention have a molecular weight generally between 1,000 and 50,000.

They are generally soluble in at least one of the three solvents consisting of water, ethanol or a water-ethanol mixture.

By evaporation of their solution, it is possible to obtain films that particularly exhibit a good affinity for hair.

In contrast with certain cation agents, they are generally compatible with nonionic derivatives used in a standard way in the preparation of compositions in gel form.

As indicated above, the formula (I) polymers exhibit attractive cosmetic properties that make it possible to use them in preparing cosmetic compositions.

This invention also has for its object cosmetic compositions characterized by the fact that they comprise at least a formula (I) polymer. These cosmetic compositions generally comprise at least an adjuvant usually used in cosmetic compositions.

The cosmetic compositions of the invention comprise formula (I) polymers either as main active ingredient or as additive.

These cosmetic compositions can be in the form of aqueous, alcohol or dilute alcohol solutions (the alcohol particularly being a lower alkanol such as ethanol or isopropanol) or in the form of emulsions, creams, lotions, powders or gels, and can be packaged as aerosols containing a propellant such as, for example, nitrogen, nitrogen protoxide or fluorocarbons of the "Freon" type.

The adjuvants generally present in the cosmetic compositions of the invention are, for example, perfumes, dyes, preservatives, sequestering agents, thickeners, filters, peptizers, emulsifiers, or again cosmetic resins usually used in hair compositions.

It should be noted that the cosmetic compositions according to the invention are both ready-to-use compositions and concentrates that have to be diluted before use. The cosmetic compositions of the invention are therefore not limited to a particular field of concentration of formula (I) polymer.

Generally, in the cosmetic compositions of the invention, the concentration of formula (I) polymers is between 0.01 and 15% by weight, particularly between 0.1 and 10% and preferably between 0.25 and 5%.

The formula (I) polymers particularly exhibit attractive cosmetic properties when they are applied to hair.

Thus, when they are applied to the hair either alone or with other active substances during a treatment such as a shampoo, dyeing, setting, brushing, permanents, etc., they notably improve the qualities of the hair.

For example, they enhance the treatment and facilitate untangling of wet hair. Even in a strong concentration, they do not give wet hair a gluey touch.

In contrast with the usual cationic agents, they do not make dry hair heavy and therefore facilitate bouffants. They give dry hair lively qualities and a glossy appearance. Untangling of dry hair is facilitated.

They effectively contribute to eliminating the defects of hair sensitized by treatments such as bleachings, permanents or dyeings. It is indeed known that sensitized hair is often dry, dull and rough and difficult to untangle and set.

In particular they offer a great advantage when they are used as pre- or post-treatment agents, particularly in the form of rinse compositions (rinses, creams or gels) applied before or after bleaching, dyeing, a permanent or shampoo.

The cosmetic compositions for hair according to the invention generally comprise at least an adjuvant usually used in cosmetic hair compositions to be able to offer them in the form of aqueous, alcohol or dilute alcohol solutions, in the form of emulsions (particularly creams), gels or powder.

The formula (I) polymers can be present in the cosmetic hair composition, either as an additive or as a main active ingredient in setting lotions, treating compositions, hairdo lotions, creams or gels, or again as an additive in shampoo, setting, setting, permament, dye compositions, restructuring lotions, seborrhea treating lotions, hair lacquers.

The cosmetic hair compositions according to the invention therefore particularly comprise:

(a) treating (or hairdo) compositions characterized in that they comprise as an active ingredient at least a formula (I) polymer.

These treating compositions can be lotions, creams or gels.

The content of these treating compositions in formula (I) polymer generally varies from 0.1 to 10% by weight, particularly from 0.25 to 5%.

The lotions are aqueous or dilute alcohol solutions of formula (I) polymers.

The pH of these lotions is close to neutrality and can vary, for example, from 5 to 8. If necessary, the pH can be brought to the desired value by adding either an acid such as citric acid or a base, particularly an alkanolamine such as monoethanolamine or triethanolamine. Generally, these lotions contain a perfume and/or a dye intended to color said lotions and/or a preservative.

To treat hair with such a lotion, said lotion is applied to wet hair, allowed to act for 3 to 15 minutes, then the hair is rinsed.

If desired, a standard setting can then be done.

The treating creams are made with a support formulated with a base of soaps or fatty alcohols in the presence of emulsifiers. The soaps can be made up from neutral or synthetic fatty acids with $C_{12}$-$C_{20}$ (such as lauric acid, myristic acid, palmitic acid, oleic acid, ricinoleic acid, stearic acid, isostearic acid and their mixtures) in concentrations between 10 and 30% and alkalizing agents (such as soda, potash, ammonia, monoethanolamine, triethanolamine and their mixtures).

Besides polymer I and soap, these creams can contain adjuvants such as fatty amides and fatty alcohols.

Of the fatty acids the following compounds in particular can be used: mono or di-ethanolamide of acids derived from copra, lauric acid, oleic acid or stearic acid in concentrations between 0 and 15%.

Of the fatty alcohols there can be used in particular lauric, oleic, myristic, cetyl, stearic, isostearic alcohols in concentrations between 0 and 25%.

Creams can also be formulated from natural or synthetic alcohols with $C_{12}$-$C_{18}$ in mixture with emulsifiers. Of the fatty alcohols there can be cited: copra alcohol, myristic alcohol, cetyl alcohol, stearyl alcohol, hydroxy stearyl alcohol in concentrations between 0.5 and 25%.

The emulsifiers can, for example, be either nonionic emulsifiers such as oxyethylenated or polyglycerolated fatty alcohols as for example oleic alcohol polyoxyethylenated with 10 to 30 moles of ethylene oxide, stearyl alcohol with 10–15 or 20 moles of ethylene oxide, oleic alcohol polyglycerolated with 4 moles of glycerol and synthetic fatty alcohols with $C_9$-$C_{15}$ polyoxyethylenated with 5 to 10 moles of ethylene oxide, these nonionic emulsifiers being present at a rate of 1 to 25% by weight, or ionic emulsifiers such as alkyl sulfates oxyethylenated or not such as sodium lauryl sulfate, ammonium lauryl sulfate, sodium cetyl stearyl sulfate, triethanolamine cetyl stearyl sulfate, monoethanolamine lauryl sulfate, sodium lauryl ether sulfate oxyethylenated (with 2.2 moles of ethylene oxide, for example) and monoethanolamine lauryl ether sulfate oxyethylenated (with 2.2 moles of ethylene oxide, for example), these latter emulsifiers being present in concentrations between 0.5 and 15% by weight.

The treating gels contain thickeners such as sodium alginate or gum arabic or cellulose derivatives in the presence or not of solvents. It is also possible to obtain a thickening of the lotions by mixing polyethyleneglycols and polyethyleneglycol stearates or distearates, or, by mixing phosphoric esters and amides, or again by mixing surfactants and solvents in an aqueous medium.

The concentration of thickener can vary from 0.5 to 30% and preferably from 0.5 to 15% by weight.

The solvents used can be lower aliphatic alcohols, glycols and their ethers. The concentration of these solvents can vary between 2 and 20%.

As indicated above, the treating compositions defined above can be used particularly before or after bleaching, dyeing, a permanent or shampoo. After an application period of 3 to 30 minutes, during which the composition is allowed to act, the hair is rinsed.

(b) shampoos characterized by the fact that they comprise at least a formula (I) polymer and at least a cationic, nonionic, anionic, amphoteric detergent or their mixture.

The cationic detergents are particularly quaternary long-chain ammoniums, alkylpyridinium salts, fatty polyether amines, imidazoline derivatives.

The nonionic detergents are particularly polyethoxylated, polypropoxylated or polyglycerated fatty alcohol ethers, polyethoxylated, polypropoxylated or polyglycerolated alkyl phenol ethers, polyethoxylated, polypropoxylated or polyglycerolated fatty acid esters, esters of polyethoxylated fatty acids and of sorbitol, polyethoxylated or polyglycerolated fatty amides.

The anionic surfactants are particularly the following compounds and their mixtures: alkaline salts, ammonium salts, amine salts or aminoalcohol salts of the following compounds:

alkylsulfates, alkylether sulfates, alkylamide sulfates and ethersulfates, alkylarylpolyethersulfates, monoglyceride sulfates, alkylsulfonates, alkylamide sulfonates, alkylaryl sulfonates, α-olefin sulfonates, alkylsulfosuccinates, alkylethersulfosuccinates, alkylamide sulfosuccinates, alkylsulfosuccinamates, alkylsulfoacetates, alkylpolyglycerol carboxylates, alkylphosphates, alkyletherphosphates, alkylsarcosinates, alkylpolypeptidates, alkylamidopolypeptidates, alkylisethionates, alkyltaurates.

The alkyl radical of all these compounds being a chain of 12 to 18 carbon atoms, fatty acids such as oleic, ricinoleic, palmitic, stearic acid, acids of copra oil or hydrogenated copra oil, carboxylic acids of polyglycol ethers answering to the formula:

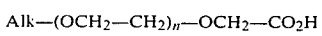

$$Alk-(OCH_2-CH_2)_n-OCH_2-CO_2H$$

where the Alk substitutent corresponds to a chain having 12 to 18 carbon atoms and where n is a whole number between 5 and 15.

The amphoteric surfactants are particularly alkylamino, mono- and di-propionates, betaines such as N-alkyl betaines, N-alkylsulfobetaines N-alkylamido betaines, cycloimidiniums such as alkylimidazolines, asparagine derivatives, the alkyl group in these surfactants designating preferably a group having between 1 and 22 carbon atoms.

These compositions in the form of shampoos can also contain various adjuvants such as, for example, perfumes, dyes, preservatives, thickeners, foam stabilizers, softeners.

In these shampoos the detergent concentration is generally between 3 and 50% by weight, and the formula (I) polymer concentration particularly between 0.1 and 5% and in particular between 0.25 and 5%.

(c) setting lotions or blow-dry lotions, particularly for sensitized hair, characterized by the fact that they comprise at least a formula (I) polymer, in aqueous, alcohol or dilute alcohol solution.

They can further contain at least another cosmetic resin. The cosmetic resins that can be used in such lotions are very varied. They are known and described in works on cosmetology. They are particularly homopolymers or copolymers such as, for example, polyvinylpyrrolidone, polyvinylpyrrolidone and vinyl acetate copolymers, crotonic acid and vinyl acetate copolymers, etc.

The concentration of formula (I) polymers in these setting lotions varies particularly between 0.1 and 5%, for example, between 0.25 and 5%, and the concentration of cosmetic resin varies approximately in the same proportions.

The pH of these setting lotions generally varies between 3 and 9 and preferably between 4.5 and 7.5.

(d) hair dye compositions characterized by the fact that they comprise at least a formula (I) polymer, at least a dye agent for hair and a support.

The support is selected to constitute either a cream or a gel.

The concentration of formula (I) polymers in these dye compositions varies preferably between 0.5 and 15%.

In case of an oxidation dye, the dye composition is packaged in two parts, but in a package comprising the mode of use, the second part being hydrogen peroxide. The two parts are mixed at the time of use.

When the dye compositions are creams, they comprise, beside polymer I, various ingredients permitting the presentation in the form of creams like the treatment creams defined above, to which are added an alkalizing agent and dyes.

The pH of these compositions is generally between 8 and 11 and can be regulated by addition of a suitable alkalizing agent in the dye support for example by addition of ammonia, monoethanolamine, diethanolamine or triethanolamine.

The dyes belong to the class of oxidation dyes to which can be added direct dyes such as azoics, anthraquinones, nitro derivatives of the benzene series, indamines, indoanilines, indophenols, or other oxidative dyes such as leukoderivatives of these compounds.

Said "oxidation dyes" are aromatic compounds of the diamine, aminophenol or phenol type. These aromatic compounds are dye precursors which are transformed into dye compounds by condensation in the presence of a great excess of oxidant, generally hydrogen peroxide. In oxidation dyes there are distinguished, on the one hand, "bases" which are diamines or aminophenols (ortho or para derivatives) and, on the other hand, "modifiers" which are m-diamines, m-aminophenols or polyphenols.

When the dye compositions are gelable liquids, they contain, besides formula (I) polymer and dyes or dye precursors, either polyoxyethylenated or polyglycerolated nonionic derivatives, and solvents, or soaps of liquid fatty acids such as those of oleic or isostearic acid, and solvents. The soaps are soda, potash, ammonium or mono-, di- or tri-ethanolamine soaps.

(e) hair lacquers characterized by the fact that they comprise an alcohol or dilute alcohol solution of a usual cosmetic resin for lacquers and at least a formula (I) polymer, this solution being possibly placed in an aerosol container and mixed with a propellant.

It is possible, for example, to obtain an aerosol lacquer according to the invention by adding the usual cosmetic resin and formula (I) polymer to a mixture of an anhydrous aliphatic alcohol such as ethanol or isopropanol and a propellant or a mixture of liquified propellants such as halogenated hydrocarbons of the trichlorofluoromethane or dichlorodifluoromethane type.

In these hair lacquer compositions, the concentration of cosmetic resin generally varies between 0.5 and 3% by weight, and the concentration of formula (I) polymer generally varies between 0.1 and 5% and particularly between 0.25 and 3% by weight.

Of course, it is possible to add to these hair lacquers according to the invention adjuvants such as dyes, plasticizers or any other usual adjuvant;

(f) restructuring treating lotions characterized by the fact that they comprise at least an agent having hair restructuring properties and at least a formula (I) polymer.

Restructuring agents that can be used in such lotions are, for example, methylol derivatives described in the French patents of the applicant Nos. 1,519,979; 1,519,980; 1,519,981; 1,519,982; 1,527,085.

In these lotions, the concentrations of the restructuring agent generally varies between 0.1 and 10% by weight and the concentration of the formula (I) polymer generally varies between 0.25 and 5% by weight.

(g) bleaching compositions that are made up of supports in the form of powders, solutions, emulsions or gelable liquids or creams containing at least a bleaching agent such as for example hydrogen peroxide, peroxides, solutions of persalts (persulfates, perborates, percarbonates).

Preferably, the bleaching compositions are supports in the form of creams or gelable liquids like those described above in regard to dye compositions. These supports are diluted at the time of use with a solution of hydrogen peroxide and/or peroxides and/or persalts.

They generally contain an alkalizing agent such as ammonia.

The bleaching compositions are applied according to standard techniques.

(h) permanent compositions

It is known that the standard technique for achieving permanent deformation of hair consists, in a first stage, of making openings in the S—S bonds of the hair keratin with a composition containing a reducing agent, then, after having preferably rinsed the hair, of reconstituting in a second stage said S—S bonds by applying an oxidizing composition to the hair subjected to this reduction to give the hair the desired shape.

The formulation of said reducing and oxidizing compositions is known and described in works on cosmetology, particularly by E. Sidi and C. Zviak, "Problemes Capillaires," Paris, 1966 (Gauthier-Villard).

The permanent compositions of this invention are particularly reducing compositions for the first stage of the permanent deformation operation.

The compositions contain, besides the reducing agent, adjuvants making it possible to offer them in the forms of lotions or in the form of powder to be diluted in a liquid support.

The reducing agent is most often a mercaptan such as, for example, thioglycerol or again thioglycolic acid or its derivatives.

The concentration of the reducing agent is the concentration necessary to obtain the reduction of a sufficient number of S—S bonds. These concentrations have been studied and described in works on cosmetology. For example, for thioglycolic acid the concentration is generally on the order of 1 to 11% approximately.

The pH of these compositions for the first stage of a permanent generally varies from 7 to 10.

The compositions for the second stage of a permanent contain an oxidant capable of reconstituting the reduced S—S bonds.

The permament compositions generally contain from 0.1 to 10% by weight of formula (I) polymer and particularly from 0.25 to 5%.

These lotions for the first stage of the permanent are most often aqueous solutions that can contain, in addition, pH modifiers, auxiliary reducing agents such as sulfites, solvents such as ethanol or isopropanol, surfactants, perfumes and/or dyes.

The formula (I) polymers are compatible with the ingredients and adjuvants used in permanent compositions.

The formula (I) polymers also offer attractive cosmetic properties when they are applied to the skin.

Particularly, they give the skin a softness that is noticeable to the touch.

They further offer the advantage of being compatible with the ingredients used to making skin cosmetic compositions.

The cosmetic compositions according to the invention can be cosmetic compositions for the skin, characterized by the fact that they comprise at least a formula (I) polymer.

Further, they generally comprise at least an active ingredient or adjuvant usually used in cosmetic compositions for the skin.

The cosmetic compositions for the skin according to the invention are, for example, in the forms of creams, lotions, emulsions, gels or aqueous, alcohol or dilute alcohol solutions.

The concentration of the formula (I) polymer in these compositions for the skin generally varies between 0.1 and 10% by weight and particularly from 0.25 to 5%.

The adjuvants generally present in these cosmetic compositions are, for example, perfumes, dyes, preservatives, thickeners, sequestering agents, emulsifiers, etc.

These skin compositions particularly constitute treating creams or lotions for the hands or face, antisolar creams, colored creams, cleansing creams, bath foam liquids, aftershave lotions, toilet waters, shaving foams, makeup sticks, colored or uncolored sticks particularly for lips, for makeup or for body hygiene, or again deodorant compositions.

These compositions are prepared by the usual methods.

The aftershave lotions and toilet waters are in the form of dilute alcohol solutions containing preferably a lower alkanol comprising 1 to 4 carbon atoms, such as, preferably, ethanol or isopropanol and comprising adjuvants usually used such as softening agents, cicatrizing agents, perfumes, etc.

When the composition is in the form of a shaving foam, it generally contains soaps to which optionally have been added fatty acids, foam stabilizers, softeners such as glycerin, etc.

It can be packaged in an aerosol device in the presence of propellant gases according to well known techniques.

The compositions of the invention can also be supports or bases in the form of aqueous or dilute alcohol solution, cream, gel, dispersion, emulsion for cosmetic formulations for skin treatment.

The compositions of the invention can also be used in treating nails and particularly constitute nail cleaning and polishing compositions or nail polish. They contain at least an active ingredient and at least an adjuvant usually present in compositions for nail care.

The formula (I) polymers can be present in cosmetic compositions for the skin according to the invention either as an additive or as main ingredient in treating creams and lotions for the hands and face, or again as additive in compositions of antisolar creams, colored creams, cleansing lotions, foaming oils or liquids for baths, etc.

This invention particularly has for its object cosmetic compositions as defined above comprising at least any of formula (I) polymers described below in the experimental part.

The invention also has for its object a cosmetic treatment process characterized by the fact that at least a formula (I) polymer is applied to the hair, skin or nails with a cosmetic composition with a base of polymer (I) as defined above.

In particular, the invention has for its object a process of dyeing or bleaching the hair, principally characterized by the fact that there is applied to the hair a dyeing or bleaching composition as defined above, possibly containing dyes and possibly mixed with an oxidant such as hydrogen peroxide, the composition, after being applied, it allowed to act for sufficient time to obtain the desired dyeing or bleaching effect, then the hair is rinsed.

Generally, the composition is allowed to act for 5 to 45 minutes and preferably for 15 to 30 minutes.

The amounts of dye or bleaching composition applied to the hair are generally between 10 and 100 g approximately.

According to another embodiment of the cosmetic treatment process of this application, the invention also has for its object a process of permanent deformation of the hair, characterized by the fact that a sufficient amount of a reducing composition as defined above is applied to the hair, it is allowed to act for about 5 to 20 minutes, the hair is rinsed, a sufficient amount of oxidizing composition to reform the S—S bonds of the hair keratin is applied to the hair that has been thus reduced.

The oxidizing agent is generally hydrogen peroxide or a persalt.

Generally, the hair is subjected to an extension realized particularly by putting up in curlers preferably done before application of the reducing composition.

After application of the oxidizing composition for a sufficient period, the extension of the hair is eliminated, then rinsed. Then setting can be done.

According to another embodiment, the cosmetic treatment process of this application is characterized by the fact that there is applied to the hair, particularly before or after dyeing, bleaching, a permanent or a shampoo, a treating composition as defined above, which is allowed to act for about 3 to 15 minutes, then the hair is rinsed.

The following examples illustrate the invention without, however, limiting it.

EXAMPLES OF PREPARATION

EXAMPLE 1

Preparation of a formula (I) polyer with $A_1 = A_2 = -(CH_2)_3-$, $R_1 = R_2 = R_3 = R_4 = CH_3$,

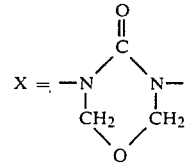

$A_3 = -(CH_2)_6-$ et $Z^\ominus = Cl^\ominus$

There are heated with reflux for 3 hours with stirring:
40.88 g (0.15 mole) of 3,5-bis(3-dimethylaminopropyl)-4-oxo-1,3,5-tetrahydrooxadiazine,
23.25 g (0.15 mole) of 1,6-dichlorohexane and
50 g of water.

It is allowed to cool and the final concentration of the solution is adjusted to 50% (weight/weight).

Chloride content: 100% of theory.

EXAMPLES 2 AND 3

Preparation of a formula (I) polymer

There were obtained in a similar way formula (I) polymers for which $R_1$, $R_2$, $R_3$, $R_4$, $A_1$, X and Z are defined as in example 1 and:

$A_3$ represents $-CH_2-CHOH-CH_2$ (example 2), $A_3$ represents $-CH_2-CH=CH-CH_2-$ (example 3).

Chloride content:
example 2: 96% of theory,
example 3: 95% of theory.

EXAMPLE 4

Formule (I) polymer for which $A_1$, $A_2$, X and Z are defined as in example 1, and $R_1=R_2=R_3=R_4=C_2H_5$ and
$A_3=-(CH_2)_6-$.

There were heated with reflux for 3 hours with stirring:
55 g (0.192 mole) of 1,3-bis(3-diethylaminopropyl)urea
29.76 g (0.192 mole) of 1,6-dichlorohexane, and
50 g of water.

It was allowed to cool and 38.4 g (0.384 mole) of formaldehyde in aqueous solution at 30% and 4 cc of concentrated hydrochloric acid were added. Heating was conducted at 95° C. for one hour. It was allowed to cool and the final concentration of the solution was adjusted to 50% (weight/weight).

Chloride content: 100% of theory.

EXAMPLES 5 TO 7

In a similar way formula (I) polymers were obtained for which $R_1$, $R_2$, $R_3$, $R_4$, $A_1$, $A_2$, X and Z are defined as in example 4 and:
$A_3$ represents $-CH_2-CHOH-CH_2-$
(example 5; chloride 90% of theory),
$A_3$ represents $-CH_2-CH=CH-CH_2-$
(example 6; chloride 97% of theory),
$A_3$ represents $-(CH_2)_2-O-(CH_2)_2-$
(example 7; chloride 99% of theory).

EXAMPLE 8

Formula (I) polymer for which:

$R_1$, $R_2$, $R_3$, $R_4$, $A_1$, $A_2$ and X are defined as in example 1,
$Z^\ominus = Br^\ominus$ and
$A_3$ represents the p-xylylenyl group.

There were heated with reflux for 3 hours
32.64 g (0.12 mole) of 3,5-bis(3-dimethylaminopropyl)-4-oxo-1,3,5-tetrahydrooxadiazine,
31.7 g (0.12 mole) of 1,4-bis(bromomethyl)benzene and
150 g of methanol.

At the end of the reaction, it was allowed to cool, then the solvent was distilled under low pressure. The final product was obtained, after dissolution in water, in the form of a 50% aqueous solution (weight/weight).

Bromide content: 100% of theory.

EXAMPLE 9

Formula (I) polymer for which $R_1$, $R_2$, $R_3$, $R_4$, $A_1$, $A_2$ and Z are defined as in example 1,
$X=NH-SO_2-NH-$, and
$A_3=-(CH_2)_2-O-(CH_2)_2-$ There were heated with reflux for 3 hours with stirring:
26.6 g (0.1 mole) of 1,3-bis(3-dimethylaminopropyl)sulfamide, and
14.3 g of dichlorodiethylether,
in 30 g of water.

It was allowed to cool and the final concentration of the solution was adjusted to 50% (weight/weight).

Chloride content: 100% of theory.

EXAMPLE 10

Formula (I) polymer for which:

$A_1=A_2=-(CH_2)_2-$, $R_1=R_2=R_3=R_4=CH_3$,
$X=-O-CO-NH-(CH_2)_6-NH-CO-O-$,
$A_3=-(CH_2)_6-$, and
$Z^\ominus = Cl^\ominus$ There were heated with reflux for 10 hours with stirring:
34.6 g (0.1 mole) of 1,6-bis(2-dimethylamino ethoxycarbonyl amino) hexane,
15.5 g (0.1 mole) of 1,6-dichlorohexane, and
50 g of water.

It was allowed to cool and the final concentration of the solution was adjusted to 50% (weight/weight).

Chloride content: 98% of theory.

EXAMPLES 11 AND 12

In a similar way the following formula (I) polymers were obtained for which $R_1$, $R_2$, $R_3$, $R_4$, $A_1$, $A_2$, X and Z are defined as in example 10, and
$A_3$ represents $-(CH_2)_2-O-(CH_2)_2-$
(example 11; chloride 100% of theory),
$A_3$ represents $-CH_2-CHOH-CH_2-$
(example 12; chloride 100% of theory).

EXAMPLE 13

Formula (I) polymer for which:

$R_1$, $R_2$, $R_3$, $R_4$, $A_1$, $A_2$, X and Z are defined as in example 10, and
$A_3$ represents $-CH_2-CH_2-(-OCH_2CH_2-)-_{5.4}$ There were heated with reflux for 9 hours with stirring:
51.9 g (0.15 mole) of 1,6-bis(2-dimethylamino ethoxycarbonylamino) hexane,
50.55 g of α,ω-dichloropolyethyleneglycol (deriving from polyethyleneglycol "300"), and
50 g of water.

It was allowed to cool and the final concentration of the solution was adjusted to 50% (weight/weight).

Chloride content: 100% of theory.

EXAMPLES 14 TO 16

In a similar way formula (I) polymers were obtained for which:

$R_1$, $R_2$, $R_3$, $R_4$, $A_1$, $A_2$ and Z are defined as in example 10, and

EXAMPLE 14

X is defined as in example 10, and $A_3$ represents $-CH_2CH_2-(-OCH_2CH_2-)-$(chloride 100% of theory).

EXAMPLE 15

X represents

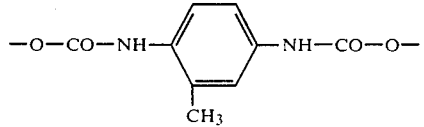

and $A_3$ is defined as in example 13 (chloride 99% of theory).

EXAMPLE 16

X is defined as in example 15 and $A_3$ represents $-CH_2CH_2-OCH_2CH_2)$ (chloride 100% of theory).

EXAMPLE 17

Formula (I) polymer for which:

$R_1=R_2=R_3=R_4=CH_3$
$A_1=CH_2$, $A_2=(CH_2)_2$,

X represents —CO—NH—
A₃ represents —(CH₂)₃—, and $Z^\theta = Cl^\theta$

There were heated with reflux for 60 hours 0.1 mole of N,N-dimethyl N',N'-dimethyl 1,3-diamino propane and 0.1 mole of N-(β-chloroethyl) chloroacetamide in 20 cc of water. The resulting aqueous solution had a $Cl^\theta$ content of 93% of theoretical value.

EXAMPLE 18

Formula (I) polymer for which:

$R_1 = R_2 = CH_3$, $R_3 = R_4 = C_2H_5$ and
$A_1$, $A_2$, X, $A_3$ and Z are defined as in example 17.

The operation was similar to that of example 17.

The $Cl^\theta$ content of the aqueous solution was 94% of theoretical value.

EXAMPLE 19

Formula (I) polymer for which:

$R_1 = R_2 = R_3 = R_4 = C_8H_{17}$,
$A_1 = A_2 = (CH_2)_2$,
$Z^\theta$ represents $Cl^\theta$
X represents —CO—NH—C—(CH₃)₂—(C-H₅—C(CH₃)₂—NH—CO—
and A₃ represents —CH₂CH₂(OCH₂CH₂)₇—

There were heated in 40 cc of methanol 0.1 mole of diamine

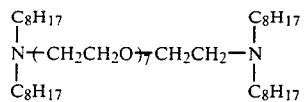

and 0.1 mole of dihalide

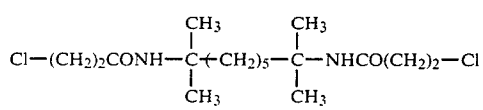

At the end of the reaction the solvent was evaporated, the residue washed with acetone and dried.

The resulting polymer had a value in $Cl^\theta$ equal to 89% of theoretical value.

EXAMPLE 20

Formula (I) polymer for which:

$R_1 = R_2 = R_3 = R_4 = CH_3$,
$A_1 = A_2 = CH_2$,
$Z^\theta = Cl^\theta$,
X represents —CO—NH—C(C₄H₉)₂—(CH₂)₅—C(C₄H₉)₂—NH—CO—
and A₃ represents —CH₂CH₂(OCH₂CH₂)₇—

The operation was similar to that of example 19.

The resulting polymer had a $Cl^\theta$ content equal to 92% of theoretical value.

EXAMPLE 21

Formula (I) polymer for which:

$R_1 = R_2 = R_3 = R_4 = CH_3$,
$A_1 = A_2 = —(CH_2)_3—$
X = —NHCONH—
A₃ represents —(CH₂)₂—CO—NH—C(CH₃)₂—(CH₂)₅—C(CH₃)₂—NH—CO—(CH₂)₂—
$A_1 = A_2 = —(CH_2)_2—$,
or else X = —CO—NH—C(CH₃)₂—(CH₂)₅—C(CH₃)₂—NH—CO—
and A₃ represents —(CH₂)₃—NHCONH—(CH₂)₃,
substituents $A_3$ and $A_1XA_2$ here being interchangeable.

There were heated with reflux in 50 cc of methanol 0.1 mole of diamine

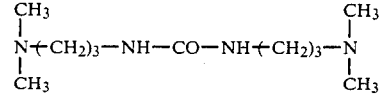

and 0.1 mole of dichloride:

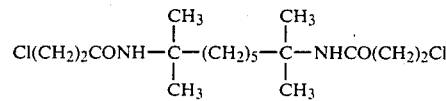

After evaporation of the solvent, the residue was washed in ethyl ether and dried. The resulting polymer had a $Cl^\theta$ content equal to 94% of theoretical value.

The following polymers were prepared in a similar way:

| EXAMPLE No | Polymer containing following repeated groups | chloride content % of theory |
|---|---|---|
| 22 | —N⁺(CH₃)₂—(CH₂)₃—NHCONH(CH₂)₃—N⁺(CH₃)₂—CH₂CONH—C(C₄H₉)₂—(CH₂)₁₀—C(C₄H₉)₂—NHCO—CH₂—   2Cl⁻ | 94.5 |
| 23 | —N⁺(CH₃)₂—(CH₂)₂NHCONH(CH₂)₂—N⁺(CH₃)₂—CH₂CONH—C(CH₃)₂—(CH₂)₆—C(CH₃)₂—NHCOCH₂—   2Cl⁻ | 93 |
| 24 | —N⁺(CH₃)₂—(CH₂)₃NHCONH(CH₂)₃—N⁺(CH₃)₂—CH₂CONH—C(CH₃)₂—(CH₂)₁₀—C(CH₃)₂—NHCOCH₂—   2Cl⁻ | 96.5 |

| EXAMPLE No | Polymer containing following repeated groups | chloride content % of theory |
|---|---|---|
| 25 | 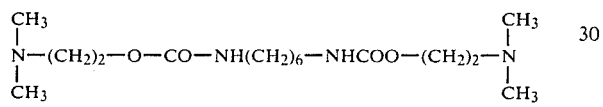 | 92.1 |

It is noted that, as in example 21, substituents —A₁, XA₂— and —A₃— in the groups of polymers of examples 22 to 25 are interchangeable.

EXAMPLE 26

Formula (I) polymer with $R_1 = R_2 = R_3 = R_4 = CH_3$
one of the substituents —A₁XA₂—
and A₃ represents —(CH₂)₂—O—CONH(CH₂)₆—N-H—COO—(—CH₂)₂—
and the other represents —CH₂—CO—N-H—C(C₄H₉)₂—(CH₂)₄—C(C₄H₉)₂—N-H—CO—CH₂—
(A₁XA₂- and A₃ being interchangeable here)
and $Z^\ominus = Cl^\ominus$.

There were heated with reflux in 50 cc of methanol 0.1 mole of diamine:

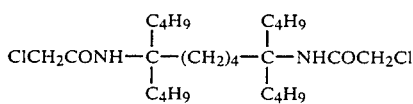

and 0.1 mole of dichloride:

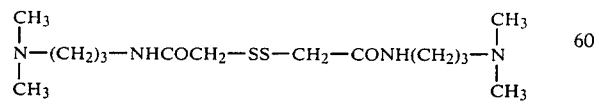

At the end of the reaction, the solvent was evaporated under low and the residue was washed in isopropyl ether then dried.

The resulting polymer had a $Cl^\ominus$ content equal to 94% of the theoretical value.

EXAMPLE 27

Formula (I) polymer with:

$R_1 = R_2 = R_3 = R_4 = CH_3$,
$A_1 = A_2 = (CH_2)_3$,
X represents —NH—CO—CH₂—S—S—CH₂—CO—NH—,
$A_3 = (CH_2)_6$ and $Z^\ominus = Br^\ominus$ There was heated with reflux for 20 hours in 30 cc of water a mixture of:

25.8 g of diamine $$\underset{CH_3}{\overset{CH_3}{\text{N}}}-(CH_2)_3-NHCOCH_2-SS-CH_2-CONH(CH_2)_3-\underset{CH_3}{\overset{CH_3}{\text{N}}}$$

19.5 g of 1,6-dibromohexane.

The water was evaporated under low pressure and the residue was washed with acetone and dried.

The resulting polymer had a $Br^\ominus$ content equal to 100% of theoretical value.

EXAMPLE 28

Formula (I) polymer with:

$R_1 = R_2 = R_3 = R_4 = CH_3$,
A₃ represents —CH₂—C₆H₄—C₆H₄—CH₂ (para),
$A_1 = A_2 = (CH_2)_3$,
X represents

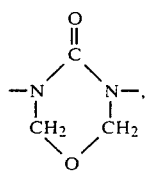

and $Z^\ominus = Cl^\ominus$.

There were heated with reflux for 12 hours with stirring:
13.6 g (0.05 mole) of 3,5-bis(3-dimethylaminopropyl)-4-oxo-1,3,5-tetrahydrooxadiazine,
12.55 g (0.05 mole) of 4,4'-bis-chloromethyl biphenyl, and
100 cc of methanol.

At the end of the reaction, it was allowed to cool then the solvent was distilled under low pressure. The residue was washed in dichloromethane and dried.

The resulting polymer had a chloride content of 82% of theoretical value.

EXAMPLE 29

In a similar way a formula (I) polymer was obtained for which:

$R_1 = R_2 = R_3 = R_4 = CH_3$,
$A_1 = A_2 = -CH_2-C(CH_3)_2-CH_2-$,
X = —NH—SO₂—NH—,
A₃ represents —CH₂—C₆H₄—C₆H₄—CH₂— (para),
and $Z^\ominus = Cl^\ominus$.

Chloride content: 87% of theoretical value.

EXAMPLE 30

Formula I polymer for which:

$R_1 = R_2 = R_3 = R_4 = CH_3$,
$A_1 = A_2 = -CH_2-C(CH_3)_2-CH_2-$,
X = —NH—SO₂—NH—,
$A_3 = -CH_2CH_2-OCH_2CH_2-OCH_2CH_2-$
and $Z^\ominus = Cl^\ominus$.

There were heated with reflux for 5 hours with stirring, 32.2 g (0.1 mole) of 1,3-bis-(2,2-dimethyl-3-dimethylaminopropyl)sulfamide, 18.7 g (0.1 mole) of 1,2-bis-(2 chloroethoxy)ethane and 50 g of water. It was allowed to cool and the final concentration of the solution was adjusted to 50% (weight/weight).

Chloride content: (% of theory): 80.

EXAMPLES 31 TO 34

Mixtures of dihalides and diamines (equimolecular proportions of dihalide and diamines) were made to react in a mode of operation similar to that described above. The following dihalides and diamines were used:

$$A_c: \underset{CH_3}{\underset{|}{N}}-CH_2-C(CH_3)_2-CH_2-NH-SO_2-$$
$$-NH-CH_2-C(CH_3)_2-CH_2-\underset{CH_3}{\underset{|}{\overset{CH_3}{\overset{|}{N}}}}$$

$$A_d: \underset{CH_3}{\underset{|}{\overset{CH_3}{\overset{|}{N}}}}-CH_2-CHOH-CH_2-\underset{CH_3}{\underset{|}{\overset{CH_3}{\overset{|}{N}}}}$$

$$A_e: \underset{CH_3}{\underset{|}{\overset{CH_3}{\overset{|}{N}}}}-(CH_2)_3-N\underset{CH_2}{\overset{\overset{O}{\overset{\|}{C}}}{\diagup\diagdown}}N-(CH_2)_3-\underset{CH_3}{\underset{|}{\overset{CH_3}{\overset{|}{N}}}}$$

$$A_b: \underset{CH_3}{\underset{|}{\overset{CH_3}{\overset{|}{N}}}}-(CH_2)_3-\underset{CH_3}{\underset{|}{\overset{CH_3}{\overset{|}{N}}}}$$

$B_b$: Cl—(CH$_2$)$_6$—Cl

| Example No | Quaternary polymers prepared from (moles) | Chloride content (% of theory) |
|---|---|---|
| 31 | (½) A$_c$ + (½) A$_b$ + (1) B$_b$ | 90 |
| 32 | (¼) A$_c$ + (¾) A$_b$ + (1) B$_b$ | 90 |
| 33 | (¾) A$_c$ + (¼) A$_b$ + (1) B$_b$ | 95 |
| 34 | (½) A$_c$ + (½) A$_d$ + (1) B$_b$ | 96 |

EXAMPLES 35 TO 53

The following formula I polymers were prepared by operating in a way similar to that described in the previous examples:

EXAMPLE 35

Formula I polymer for which
$R_1=R_2=R_3=R_4=$methyl
$A_1=A_2=(CH_2)_3$; X=—NH—CO—CO—NH—
$A_3=$—CH$_2$CH$_2$—OCH$_2$CH$_2$—OCH$_2$CH$_2$—
and $Z^\theta=Cl^\theta$.
Chloride content: 95.5% of theory.

EXAMPLE 36

Formula I polymer for which
$R_1$-$R_4$, $A_1$, $A_2$, X and Z are defined as in example 35, and $A_3=(CH_2)_6$
Chloride content: 95.4% of theory.

EXAMPLE 37

Formula I polymer for which
$R_1$-$R_4$, $A_1$, $A_2$, X and Z are defined as in example 35, and $A_3=$—CH$_2$—C$_6$H$_4$—C$_6$—H$_4$—CH$_2$— (para)
Chloride content: 86% of theory.

EXAMPLE 38

Formula I polymer for which
$A_1$, $A_2$, $A_3$, X and Z are defined as in example 37, and $R_1=R_2=R_3=R_4=$ethyl
Chloride content: 85.5% of theory.

EXAMPLE 39

Formula I polymer for which
$R_1$-$R_4$, $A_1$, $A_2$, $A_3$ and Z are defined as in example 37, and X=—NH—CO—NH—
Chloride content: 87.5 of theory.

EXAMPLE 40

Formula I polymer for which
$R_1$, $R_2$, $R_3$, $R_4$, $A_1$, $A_2$, X and Z are defined as in example 39,
and $A_3=$—CH$_2$—C$_6$H$_4$—O—C$_6$H$_4$—CH$_2$ (para).
Chloride content: 94% of theory.

EXAMPLE 41

Formula I polymer for which
$R_1=R_2=R_3=R_4=CH_3$,
$A_1=A_2=(CH_2)_3$,
X represents:

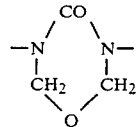

$A_3$ represents —CH$_2$—CO—NH—C(CH$_3$)$_2$—(CH$_2$)$_4$—C(CH$_3$)$_2$—NH—CO—CH$_2$—
and $Z^\theta=Cl^\theta$
$Cl^\theta$ content: 93.4% of theory.

EXAMPLE 42

Formula I polymer for which
$R_1$, $R_2$, $R_3$, $R_4$, $A_1$, X, $A_2$ and Z are defined as in example 41,
and $A_3$ represents —(CH$_2$)$_2$13 CO—NH—C(CH$_3$)$_2$—(CH$_2$)$_6$—C(CH$_3$)$_2$—NH—CO—(CH$_2$)$_2$—
$Cl^\theta$ content: 98.5% of theory.

EXAMPLE 43

Formula I polymer for which
$R_1$, $R_2$, $R_3$, $R_4$, $A_1$, $A_2$ and Z are defined as in example 41,
X represents —NH—CO—NH—,
$A_3$ represents —(CH$_2$)$_2$—NH—CO—(CH$_2$)$_4$—CO—NH—(CH$_2$)$_2$—
$Cl^\theta$ content: 94.3% of theory.

EXAMPLE 44

Formula I polymer for which
$R_1=R_2=R_3=R_4=CH_3$, $A_1=A_2=(CH_2)_2$,
X represents —O—CO—NH—(CH$_2$)$_6$—NH—CO—O—
$A_3$ represents: —(CH$_2$)$_2$—NH—CO—C$_6$H$_4$—C$_6$H$_4$—CO—NH—(CH$_2$)$_2$— (ortho)
and $Z^\theta=Cl^\theta$.
$Cl^\theta$ content: 94.2% of theory.

EXAMPLE 45

Formula I polymer for which $R_1=R_2=R_3=R_4=CH_3$, $A_1=A_2=$—$CH_2$—$C(CH_3)_2$—$CH_2$—,
X represents —NH—CO—$(CH_2)_4$—CO—NH—,
$A_3$ represents —$(CH_2)_2$—NH—CO—NH—$(CH_2)_2$—
and $Z^\ominus = Cl^\ominus$.
$Cl^\ominus$ content: 99% of theory.

EXAMPLE 46

Formula I polymer for which $R_1=R_2=R_3=R_4=C_8H_{17}$
$A_1=A_2=CH_2$
X represents —CO—NH—$C(CH_3)_2$—$(CH_2)_6$—$C(CH_3)_2$—NH—CO—
$A_3$ represents —$(CH_2)_2$—NH—CO—$C_6H_4$—$C_6H_4$—CO—NH (ortho)
and $Z^\ominus = Cl^\ominus$.
$Cl^\ominus$ content: 90% of theory.

EXAMPLE 47

Formula I polymer for which $R_1=R_2=R_3=R_4=CH_3$; X = —S—S—
$A_1=A_2=(CH_2)_2$
$A_3=(CH_2)_4$—O—CO—$C_6H_4$—CO—O— (para)
and $Z^\ominus = Cl^\ominus$.
$Cl^\ominus$ content: 99% of theory.

EXAMPLE 48

Formula I polymer for which $R_1=R_2=R_3=R_4=C_2H_5$
$A_1=A_2=(CH_2)_3$
X represents —NH—CO—CO—NH—
$A_3$ represents —$(CH_2)_3$—O—CO—$(CH_2)_6$—CO—O—$(CH_2)_3$
and $Z^\ominus = Cl^\ominus$.
$Cl^\ominus$ content: 84% of theory.

EXAMPLE 49

Formula I polymer for which $R_1=R_2=R_3=R_4=CH_3$
$A_1=A_2=$—$(CH_2)_2$—$C(CH_3)_2$—
X represents —NH—CO—$C_6H_4$—CO—NH (para)
$A_3$ represents —$CH_2$—COO—$(CH_2)_3$
and $Z^\ominus = Cl^\ominus$
$Cl^\ominus$ content: 80% of theory.

EXAMPLE 50

Formula I polymer for which $R_1=R_2=R_3=R_4=CH_3$
$A_1=A_2=$—$CH_2$—$C(CH_3)_2$—$CH_2$—
X = —O—CO—$(CH_2)_4$—CO—O—
$A_3 =$ —$CH_2$—CONH—$CH_2$—$CH_2$—
and $Z^\ominus = Cl^\ominus$.
$Cl^\ominus$ content: 82% of theory.

EXAMPLE 51

Formula I polymer for which $R_1R_2=C_2H_5$
$R_3=R_4=CH_3$
$A_1=CH_2$, $A_2=(CH_2)_3$, X = —CO—NH,
$A_3 =$ —$CH_2$—CO—O—$(CH_2)_4$—O—CO—$CH_2$—
and $Z^\ominus = Cl^\ominus$.
$Cl^\ominus$ content: 84% of theory.

EXAMPLE 52

Formula I polymer for which $R_1$, $R_2$, $R_3$, $R_4$, $A_1$ and $A_2$ are defined as in example 51
X represents —CO—O—
$A_3$ represents —$CH_2$—CO—O—$(CH_2)_4$—O—CO—$CH_2$—
and $Z^\ominus = Cl^\ominus$.
Chloride content: 81% of theory.

EXAMPLE 53

Formula I polymer for which $R_1=R_2=R_3=R_4=C_4H_9$
$A_1=A_2=CH_2$, X = —CO—O—$(CH_2)_4$—O—CO—
$A_3 =$ —$(CH_2)_2$—NH—CO—$(CH_2)_4$—CO—NH—$(CH_2)_2$—
and $Z^\ominus = Cl^\ominus$.
Chloride content: 86% of theory.

EXAMPLES OF EMBODIMENT AND USE OF COSMETIC COMPOSITIONS

Example C1: Oxidation dye

| | |
|---|---|
| triethanolamine lauryl sulfate at 40% of active material | 2.5 g |
| 2-octyl dodecanol marketed under the name EUTANOL G by Henkel company | 7.5 g |
| oleic diethanolamide | 7 g |
| oleocetyl alcohol at 30 moles of EO marketed under the name MERGITAL OC 30 by the Henkel company | 3 g |
| oleic acid | 20 g |
| polymer of example 35 | 2.5 g |
| benzyl alcohol | 10 g |
| ethyl alcohol at 96° | 10 g |
| ammonia at 22° Be | 16 ml |
| N,N—bis-(2-hydroxyethyl) paraphenylene diamine sulfate | 1 g |
| p-aminophenol | 0.4 g |
| resorcin | 0.15 g |
| m-aminophenol | 0.10 g |
| alphanaphthol | 0.04 g |
| hydroquinone | 0.10 g |
| ethylenediaminetetraacetic acid | 0.24 g |
| sodium bisulfite (d = 1.32) | 1 ml |
| water sufficient for | 100 g |

There are mixed in a bowl 30 g of this support with 30 g of hydrogen peroxide at 20 volumes. A gel that is consistent, pleasant to apply and which adheres well to the hair is obtained.

It is applied with a brush. It is allowed to set for 30 to 40 minutes then rinsed.

The hair is easy to untangle. Touch is silky. The hair is set and dried. The hair is glossy, lively and has body (volume); the touch is silky and untangling is easy.

A LIGHT BLOND shade is obtained.

Example C2: Oxidation dye

| | |
|---|---|
| R—O—$(C_2H_3O)$ $(CH_2OH)\overline{}_nH$<br>R = oleic<br>n statistical value = 2 | 25 g |
| R—O—$(C_2H_3)$ $(CH_2OH)\overline{}_nH$<br>R = oleic<br>n statistical value = 4 | 20 g |
| 96° ethyl alcohol | 10 g |
| butylglycol | 6 g |
| polymer of example 18 | 3 g |
| ammonia at 22° Be | 15 ml |
| N,N—bis(2-hydroxyethyl) paraphenylene diamine sulfate | 1 g |
| p-aminophenol | 0.4 g |

-continued

| | |
|---|---|
| resorcin | 0.10 g |
| m-aminophenol | 0.10 g |
| alphanaphthol | 0.40 g |
| hydroquinone | 0.10 g |
| ethylenediaminetetraacetic acid | 0.24 g |
| sodium bisulfite (d = 1.32) | 1 ml |
| water sufficient for | 100 g |

The operation is as in the preceding example and similar results are obtained.

Example C3: Oxidation dye

| | |
|---|---|
| cetylstearyl alcohol | 18 g |
| 2-octyl dodecanol marketed under the name of EUTANOL G by Henkel company | 3 g |
| stearyl alcohol oxyethylenated with 15 moles of EO | 3 g |
| ammonium lauryl sulfate (with 30% active material) | 12 g |
| polymer of example 36 | 3 g |
| ammonia at 22° Be | 13 ml |
| 1-amino (2-methoxy ethyl) 4-amino benzene dihydrochlorate | 1.6 g |
| p-aminophenol | 0.3 g |
| resorcin | 0.2 g |
| m-aminophenol | 0.25 g |
| N—(2-hydroxy ethyl) 5-amino 2-methyl phenol | 0.02 g |
| 1-(2-hydroxy ethyloxy) 2,4-diamino benzene dihydrochlorate | 0.02 g |
| ethylenediaminetetraacetic acid sold under the name of TRILON B | 0.20 g |
| sodium bisulfite (d = 1.32) | 1 ml |
| water sufficient for | 100 g |

There are mixed in a bowl 30 g of this formula with 45 g of 20 volume hydrogen peroxide.

A smooth cream, pleasant to apply and which adheres well to the hair is obtained.

The cream is applied to the hair with a brush.

It is allowed to set for 30 minutes then rinsed. The hair easily untangles and the touch is silky.

The hair is set and dried.

The hair is glossy, lively and has volume, the touch is silky and untangling is easy.

A LIGHT BROWN shade is obtained.

Example C4: Oxidation dye

| | |
|---|---|
| cetyl stearyl alcohol | 12 g |
| stearyl alcohol oxyethylenated with 15 moles of EO | 7 g |
| stearic acid | 2 g |
| sodium cetylstearyl sulfate | 2 g |
| ammonium lauryl sulfate (with 30% active material) | 10 g |
| polymer of example 39 | 3 g |
| ammonia at 22° Be | 13 ml |
| 1-amino (2-methoxy ethyl) 4-amino benzene dihydrochlorate | 1.6 g |
| p-aminophenol | 0.3 g |
| resorcin | 0.2 g |
| m-amino phenol | 0.25 g |
| N—(2-hydroxy ethyl) 5-amino 2-methyl phenol | 0.02 g |
| 1-(2-hydroxy ethyloxy) 2,4-diamino benzene dihydrochlorate | 0.02 g |
| TRILON B | 0.20 g |
| sodium bisulfite (d = 1.32) | 1 ml |
| water sufficient for | 100 g |

The operation is as in the preceding example and the same results are obtained (LIGHT BROWN).

Example C5: Brightening ammonia oil

| | |
|---|---|
| 2-octyl dodecanol marketed under the name of EUTANOL G by the Henkel company | 8 g |
| triethanolamine lauryl sulfate with 40% active material | 3 g |
| oleic diethanolamide | 6 g |
| tallow amide hydrogenated with 50 moles of ethylene oxide | 3.5 g |
| oleic acid | 18 g |
| polymer of example 17 | 3 g |
| 96° ethyl alcohol | 15 g |
| propyleneglycol | 12 g |
| TRILON B | 0.3 g |
| ammonia at 22° Be | 16 ml |
| water sufficient for | 100 g |

There are mixed in a bowl before use 40 g of this formula with 40 g of 30 volume hydrogen peroxide.

A gel is obtained that is pleasant to apply and adheres well to hair on application by brush. It is allowed to stand for 30 to 45 minutes and is rinsed.

The wet hair easily untangles, the touch is silky. After drying, it is glossy, lively, has body (volume); the touch is silky and untangling easy.

The hair is in a better state than after bleaching with the same formula but without the cationic polymer.

A DARK BLOND is obtained on dark brown hair after bleaching.

Example C6: Structuring lotion

There are mixed before use:

| | |
|---|---|
| 0.2 g of dimethylol ethylene thiourea with 20 ml of a solution containing: | |
| polymer of example 27 | 1.5 g |
| triethanolamine sufficient for pH: 2.7 | |
| water sufficient for | 100 ml |

It is applied to hair that has been washed and wiped before proceeding to setting.

The hair untangles easily, the touch is silky.

The hair is set and dried.

The hair is glossy, lively, has body (volume), the touch is silky, untangling is easy.

Example C7: Hair care cream.

| | |
|---|---|
| cetylstearyl alcohol | 25 g |
| stearyl alcohol | 5 g |
| sodium cetylstearyl sulfate | 5 g |
| polymer of example 38 | 2 g |
| water sufficient for | 100 g |

This cream is applied to hair that has been cleaned, wet and wiped, in sufficient amount (60 to 80 g) to impregnate and cover the hair well.

It is allowed to stand 15 to 25 minutes then rinsed. The wet hair is very soft and easy to untangle.

It is set and dried under the dryer. The dry hair easily untangles and has a silky touch; it is glossy, lively and has volume.

Example C8: Shampoo

| | |
|---|---|
| polymer according to example 36 | 0.5 g |
| Na alkyl ($C_{12}$–$C_{14}$) ether sulfate (2.2 ethylene oxide) at 25% active material | 25 g |
| copra diethanolamide | 3 g |
| hydroxypropylmethylcellulose sold under the name Methocel F 4 M by the Dow company: active material | 0.2 g |
| perfume, preservative, dye | |

The pH of this composition is adjusted to 6.

Example C9: Shampoo

| | |
|---|---|
| polymer according to example 35: active material | 1 g |
| sodium olefin sulfonate $C_{14}C_{16}$ sold under the name Elfan 0346 by the AKZO company: active material | 20 g |
| copra diethanolamide | 3 g |
| perfume, preservative, dye | |
| water sufficient for | 100 g |

The pH of this composition is adjusted to 6.3.

Example C10: Shampoo

| | |
|---|---|
| polymer according to example 37 | 0.7 g |
| cycloimidazoline derivative of coconut oil at 38% active material sold under the name Miranol C.2 M conc. by the Miranol company | 10 g |

$$C_{11}H_{23}-C\underset{N}{\overset{\parallel}{\underset{\diagdown}{\bigg|}}}\overset{CH_2-COONa}{\underset{CH_2}{\diagup}}N\underset{\diagup}{\overset{\ominus}{\diagdown}}CH_2-CH_2-O-CH_2-COO^{\ominus}$$

| | |
|---|---|
| sodium laurylsulfate: active material | 3 g |
| copra diethanolamide | 3 g |
| water sufficient for | 100 g | the pH is adjusted to 8.8

Example C11: Shampoo

| | |
|---|---|
| polymer according to example 38 | 2 g |
| $R-(O-CH_2-CH_2)_x-OCH_2-COOH$, R being a mixture of alkyl radicals $C_{12}-C_{14}$, X equal to 10, sold under the name AKYPO RLM 100 by the Chem Y company | 12 g |
| copra diethanolamide | 2 g |
| NaCl | 3 g |
| water sufficient for | 100 g |

The pH of this composition is adjusted to 7.5.

Example C12: Shampoo

| | |
|---|---|
| polymer according to example 39: active material | 2.5 g |
| lauric alcohol polyethoxylated with 12 moles of ethylene oxide: active material | 15 g |
| lauric diethanolamide | 2 g |
| perfume, preservative, dye | |
| water sufficient for | 100 g |

The pH of this composition is adjusted to 6.2.

Example C13: Shampoo

| | |
|---|---|
| polymer according to example 18: active material | 1.5 g |
| $R-CHOH-CH_2-O-(CH_2-CHOH-CH_2-O)_n-H$: active material R = mixture of alkyl radicals of $C_9C_{12}$. n: represents an average statistical value of about 3.5. | 15 g |
| copra diethanolamide | 2.5 g |
| perfume, preservative, dye, | |
| water sufficient for | 100 g |

The pH of this composition is adjusted to 7.8.

Example C14: Rinse

| | |
|---|---|
| polymer according to example 17: active material | 0.8 g |
| lanete wax: active material | 2.5 g |
| mixture of fatty alcohols and oxyethylenated products sold under the name POLAWAX GP 200 by the Croda Ltd company: active material | 2 g |
| hydroxyethylcellulose sold under the name CELLOSIZE QP 4400 by Union Carbide company: active material | 0.8 g |
| chlorhexidine hydrochloride in powder (ICI): active material | 0.05 g |
| water, dye(s) sufficient for | 100 g |

The pH of this composition is adjusted to 6.1.

Example C15: Rinse

| | |
|---|---|
| polymer according to example 27: active material | 0.05 g |
| mixture of cetylstearyl alcohol and cetyalstearyl alcohol oxyethylenated with 15 moles of ethylene oxide sold under the name SINNOWAX AO by the Henkel company: active material | 2.5 g |
| dimethylammonium hydrogenated tallow chloride | 1.5 g |
| casein derivative sold under the name HYDAGEN P by the Henkel company | 1 g |
| chlorhexidine hydrochloride in powder (ICI) | 0.05 g |
| water, dye(s) sufficient for | 100 g |

The pH of this composition is adjusted to 6.4.

Example C 16: Reducing composition for the first stage of a permanent

| | |
|---|---|
| thioglycolic acid | 8.8 g |
| ammonia sufficient for pH = 7 | |
| ammonium carbonate | 8 g |
| cetyldimethylhydroxyethyl ammonium chloride | 0.5 g |
| polymer of example 18: active material | 3 g |
| sequestrant | 0.2 g |
| perfume | |
| dye | |
| water sufficient for | 100 g |

Example C 17: Reducing composition for permanent

| | |
|---|---|
| thioglycolic acid | 7 g |
| ammonia sufficient for pH = 7 | |
| monoethanolamine sufficient for pH = 9 | |
| polymer according to example 35: active material | 2 g |
| sequestrant | 0.2 g |
| distearyldimethylammonium chloride | 0.4 g |
| perfume sufficient | |
| dye sufficient | |
| water sufficient for | 100 g |

Example C 18: Composition for final stage of permanent

| | |
|---|---|
| thioglycolic acid | 8 g |
| ammonia sufficient for pH = 7 | |
| ammonium bicarbonate | 6.4 g |
| cetyltrimethylammonium chloride | 0.2 g |
| polymer according to example 36: active material | 1 g |
| perfume | |
| dye | |
| water sufficient for | 100 g |

The reducing compositions of example C 16 to C 18 can be used, for example, with the following hydrogen peroxide fixer:

| | |
|---|---|
| cetyldimethylhydroxy ethylammonium chloride | 0.5 g |
| phenacetin | 0.1 g |
| oxyquinoline sulfate | 0.02 g |
| citric acid | 0.3 g |
| hydrogen peroxide sufficient 20 volume | |
| dye | |
| perfume | |
| water sufficient for | 100 g |

Example C 19: Composition (fixer) for the second stage of a permanent

The following fixer can be used with a standard reducing compositions:

| | |
|---|---|
| cetyltrimethylammonium chloride | 0.2 g |
| polymer according to example 18: active material | 3 g |
| hydrogen peroxide sufficient 6 volumes | |
| phenacetin | 0.1 g |
| oxyquinoline sulfate | 0.02 g |
| citric acid | 0.3 g |
| dye | |
| perfume | |
| water sufficient for | 100 g |

Example C 20: Setting

| | |
|---|---|
| PVP/VA* E 335 | 1 g |
| polymer according to example 27 | 1 g |
| ethyl alcohol | 40 g |
| 2-amino 2-methyl 1-propanol sufficient for pH = 7 | |
| deionized water sufficient for | 100 ml |

*PVP/VA = polyvinylpyrrolidone/vinyl acetate (30%/70%)

Example C 21: Setting

| | |
|---|---|
| polymer according to example 27 | 1 g |
| dimethyl alkyl hydroxyethyl ammonium chloride (alkyl = tallow) | 0.1 g |
| ethyl alcohol | 40 g |
| 2-amino 2-methyl 1-propanol sufficient for pH = 6 | |
| deionized water sufficient for | 100 ml |

Example C 22: Setting

| | |
|---|---|
| PVP/VA S 630 (60% polyvinylpyrrolidone/40% vinyl acetate) | 0.5 g |
| polymer according to example 37 | 1 g |
| water sufficient for | 100 ml |

Example C 23: Setting

| | |
|---|---|
| 30% solution of dimethyl alkyl hydroxyethylammonium chloride (alkyl = tallow) | 0.4 g |
| polymer of example 37 | 1.2 g |
| deionized water sufficient for | 100 ml |

Example C 24: Setting

| | |
|---|---|
| PVP/VA E 335 | 1 g |
| polymer according to example 39 | 1 g |
| ethyl alcohol | 40 g |
| lactic acid sufficient for pH = 5.5 | |
| deionized water sufficient for | 100 ml |

Example C 25:

| | |
|---|---|
| polymer according to example 39 | 1.2 g |
| 30% solution of dimethyl alkyl hydroxyethylammonium chloride (alkyl: tallow) | 0.3 |
| ethyl alcohol | 40 g |
| lactic acid sufficient for pH = 5.5 | |
| deionized water sufficient for | 100 ml |

Example C 26:

| | |
|---|---|
| PVP/VA E 335 | 1 g |
| polymer of example 38 | 0.8 g |
| ethyl alcohol | 40 g |
| deionized water sufficient for | 100 ml |

Example C 27:

| | |
|---|---|
| 30% solution of dimethyl alkyl hydroxyethylammonium chloride (alkyl = tallow) | 0.35 g |
| polymer according to example 38 | 1 g |
| ethyl alcohol | 40 g |
| deionized water sufficient for | 100 ml |

Example C 28: Restructuring lotion

There is mixed before use:

| | |
|---|---|
| 0.3 g of dimethylol ethylene thiourea with 20 ml of a solution containing: | |
| polymer according to example 3: active material | 1.5 g |
| hydrochloride acid sufficient for pH 2.7 | |
| water sufficient for | 100 ml |

The mixture is applied to the hair, which has been wetted and wiped, before setting.

The hair easily untangles, the touch is silky. The hair is set and dried.

The hair is glossy, lively, had body (volume), the touch is silky, untangling is easy.

The same results are obtained by replacing the polymer of example 3 with:

| | |
|---|---|
| polymer according to example 6: active material | 1.3 g |
| pH adjusted to 2.7 with triethanolamine. | |

Example C 29: Oxidation dye

| | |
|---|---|
| triethanolamine lauryl sulfate with 40% active material | 2.5 g |
| 2-octyl dodecanol marketed under the name of EUTANOL G by the Henkel company | 7.5 g |
| oleic diethanolamide | 7 g |
| oleocetyl alcohol with 30 moles of ethylene oxide marketed under the name of MERGITAL OC 30 by the Henkel company | 3 g |
| oleic acid | 20 g |
| polymer according to example 10: active material | 2 g |
| benzyl alcohol | 10 g |

-continued

| | | |
|---|---|---|
| 96° ethyl alcohol | 11 | g |
| ammonia at 22° Be | 18 | ml |
| N,N—bis(2-hydroxy ethyl) paraphenylene diamine sulfate | 1 | g |
| p-aminophenol | 0.4 | g |
| resorcin | 0.15 | g |
| m-aminophenol | 0.10 | g |
| alphanaphthol | 0.40 | g |
| hydroquinone | 0.10 | g |
| ethylenediaminetetraacectic acid | 0.24 | g |
| sodium bisulfite (d = 1.32) | 1 | ml |
| water sufficient for | 100 | g |

There are mixed in a bowl 30 g of this support with 30 g of 20 volume hydrogen peroxide. A consistent gel is obtained that is pleasant to apply and adheres well to the hair.

It is applied with a brush.

It is allowed to stand 30 to 40 minutes then rinsed.

The hair easily untangles. The touch is silky. It is set and dried. The hair is glossy, lively, has body (volume); the touch is silky and untangling is easy.

A DARK ASH BLOND shade is obtained.

Example C 30: Oxidation dye

| | | |
|---|---|---|
| EUTANOL G (Henkel) | 8 | g |
| oleic diethanolamide | 6 | g |
| MERGITAL OC 30 (Henkel) | 2 | g |
| oleic acid | 20 | g |
| polymer according to example 14: active material | 3 | g |
| benzyl alcohol | 10 | g |
| 96° ethyl alcohol | 12 | g |
| ammonia at 22° Be | 17.5 | ml |
| p-aminophenol | 0.3 | g |
| resorcin | 0.65 | g |
| m-aminophenol | 0.65 | g |
| p-toluylene diamine | 0.15 | g |
| ethylenediaminetetraacetic acid | 0.30 | g |
| sodium bisulfite (d = 1.32) | 1.2 | ml |
| water sufficient for | 100 | g |

The operation is the same as in the above example and the same results are obtained but with a LIGHT BLOND shade.

Example C 31: Oxidation dye

| | | |
|---|---|---|
| product of the formula: —R—O—[C$_2$H$_3$O (CH$_2$OH)$_n$]H with R = oleic and n = statistical value of about 2 | 20 | g |
| product of the preceding formula with n = 4 (statistical) | 20 | g |
| oleic diethanolamide | 12 | g |
| polymer according to example 13: active material | 3 | g |
| 96° ethyl alcohol | 12 | g |
| butylglycol | 1 | g |
| propyleneglycol | 2 | g |
| pentasodium salt of diethylene triamino pentaacetic acid (40% active material) | 2.5 | g |
| ammonia at 22° Be | 9 | ml |
| 1-amino (2-methoxy ethyle) 4-amino benzene dihydrochloride | 1.6 | g |
| p-aminophenol | 0.3 | g |
| resorcin | 0.2 | g |
| m-aminophenol | 0.25 | g |
| N(2-hydroxy ethyl) 5-amino 2-methyl phenol | 0.02 | g |
| 1-(2-hydroxy ethyloxy) 2,4-diamino benzene dihydrochloride | 0.02 | g |
| sodium bisulfite (d = 1.32) | 1 | ml |
| water sufficient for | 100 | g |

The operation is as in example C 29 and the same cosmetic results are obtained with a LIGHT ASH BROWN shade.

Example C 32: Oxidation dye

| | | |
|---|---|---|
| triethanolamine lauryl sulfate with 40% active material | 2.5 | g |
| EUTANOL G (Henkel) | 7.5 | g |
| oleic diethanolamide | 7.0 | g |
| MERGITAL OC 30 (Henkel) | 3.0 | g |
| polymer according to example 28: active material | 3.0 | g |
| oleic acid | 20.0 | g |
| benzyl alcohol | 10 | g |
| 96° ethyl alcohol | 10 | g |
| ammonia at 22° Be | 18 | ml |
| N,N—bis(2-hydroxyethyl) paraphenylene diamine sulfate | 1 | g |
| p-aminophenol | 0.4 | g |
| resorcin | 0.15 | g |
| m-aminophenol | 0.10 | g |
| alphanaphthol | 0.40 | g |
| hydroquinone | 0.10 | g |
| ethylenediaminetetraacetic acid | 0.24 | g |
| sodium bisulfite (d = 1.32) | 1 | ml |
| water sufficient for | 100 | g |

There are mixed in a bowl 30 g of this support with 30 g of 20 volume hydrogen peroxide. A consistent gel is obtained which is pleasant to apply and adheres well to the hair.

It is applied with a brush. It is allowed to stand 30 to 40 minutes and rinsed.

The hair untangles easily. The touch is silky. The hair is set and dried. The hair is glossy, lively, had body (volume), the touch is silky and untangling is easy.

A DARK ASH BLOND shade is obtained.

Example C 33: Oxidation dye

| | | |
|---|---|---|
| EUTANOL G (Henkel) | 8 | g |
| oleic diethanolamide | 6 | g |
| polymer according to example 26: active material | 2.5 | g |
| benzyl alcohol | 10 | g |
| 96° ethyl alcohol | 12 | g |
| ammonia at 22° Be | 17.5 | ml |
| p-aminophenol | 0.3 | g |
| resorcin | 0.65 | g |
| m-aminophenol | 0.65 | g |
| p-toluylene diamine | 0.15 | g |
| ethylenediaminetetraacetic acid | 0.30 | g |
| sodium bisulfite (d = 1.32) | 1 | ml |
| water sufficient for | 100 | g |

The operation is as in the preceding example and the same results are obtained but with a LIGHT BLOND shade.

Example C 34: Rinse

| | | |
|---|---|---|
| polymer according to example 28 | 0.2 | g |
| potassium salt of a condensate of collagen protein and coconut fatty acid with a molecular weight of 700–800 with 30% active material sold under the name LEXEINE S.620 by the Inolex company | 2 | g |
| water sufficient for | 100 | g |

The pH is adjusted to 7.3.

This composition is applied to wet hair. After a standing time of some minutes, it is washed.

The hair easily untangles.

The hair is set and dried.

Example C 35: Shampoo

| | |
|---|---|
| polymer according to example 28 | 0.7 g |
| nonionic surfactant of the formula | 15 g |

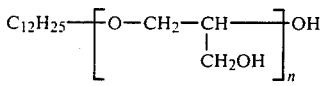

| | |
|---|---|
| with n = statistical value of 4.2 | |
| copra diethanolamide | 3 g |
| sorbitan monolaurate polyoxyethylenated with 20 moles of EO sold under the name TWEEN 20 by the Atlas company | 4 g |
| sodium chloride | 2 g |
| water sufficient for | 100 g |

The pH is adjusted to 6.3.

Example C 36: Shampoo

| | |
|---|---|
| polymer according to example 29 | 1 g |
| surfactant of the formula: R—CHOH—CH$_2$—O—(CH$_2$—CHOH—CH$_2$—O)$_n$—H R: mixture of alkyl radicals of C$_9$-C$_{12}$ n: represents an average statistical value of about 3.5 | 10 g |
| cycloimidazole derivative of coconut oil with 38% active material sold under the name "Miranol C. 2 M Conc.," by the Miranol company | 5 g |

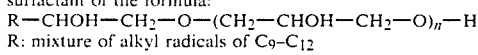

| | |
|---|---|
| lauric diethanolamide | 3 g |
| hydrolyzate of proteins derived from collagens with 55% active material sold under the name LEXEINE X.250 by the Inolex company | 3.5 g |
| methyl paraoxybenzoate | 0.3 g |
| water sufficient for | 100 g |

The pH is adjusted to 6.9.

Example C 37: Shampoo

| | |
|---|---|
| polymer according to example 29 | 2 g |
| alkyl (C$_{12}$-C$_{18}$) dimethyl ammonio acetate sold under the name DEHYTON AB 30 by the Henkel company | 15 g |
| surfactant of the formula: F—(O—CH$_2$—CH$_2$)$_x$O—CH$_2$—COOH R being a mixture of alkyl radicals C$_{12}$-C$_{14}$ x is equal to 10, with 90% active material sold under the name Akypo RLM by the Chem Y company | 5 g |
| decyl dimethylamine oxide with 30% active material sold under the name Barlox 10 S by the Lonza company | 3 g |
| copra diethanolamide | 2 g |
| sodium chloride | 2 g |
| water sufficient for | 100 g |

The pH is adjusted to 7.9 with soda.

Example C 39: Hair care cream

| | |
|---|---|
| sodium cetyl stearyl sulfate | 6 g |
| cetyl alcohol | 17 g |
| stearyl alcohol oxyethylenated with 15 moles of EO | 4 g |
| oleic alcohol | 4 g |
| compound of example 41 | 2 g |
| water sufficient for | 100 g |

The operation is as in the preceding example and the same results are obtained.

Example C 39: Hair care cream

| | |
|---|---|
| cetyl stearyl alcohol | 25 g |
| stearyl alcohol | 5 g |
| sodium cetyl stearyl sulfate | 5 g |
| compound of example 43 | 3 g |
| water sufficient for | 100 g |

This cream is applied to clean, wet, wiped hair, in sufficient amount (60–80 g) to impregnate and cover the hair well.

It is allowed to stand for 15 to 25 minutes and is rinsed. The wet hair is very soft and easy to untangle.

The hair set and dried under the drier. The dry hair easily untangles and has a silky touch, it is glossy, lively and has volume.

Example C 40: Hair care cream

| | |
|---|---|
| sodium cetyl stearyl sulfate | 6 g |
| cetyl alcohol | 17 g |
| stearyl alcohol with 15 moles of EO | 4 g |
| oleic alcohol | 4 g |
| compound of example 46 | 2 g |
| water sufficient for | 100 g |

The operation is as in the preceding example and the same results are obtained.

Example C 41: Structuring lotion

There is mixed before use:

| | |
|---|---|
| 0.25 g of dimethylol ethylene thiourea with 20 ml of a solution containing: | |
| polymer of example 44 | 1.5 g |
| hydrochloride acid sufficient for pH = 2.7 | |
| with water sufficient for | 100 ml |

The mixture is applied to hair washed and wiped before setting.

The hair easily untangles, touch is silky.

The hair is set and dried.

The hair is glossy, lively, has body (volume), touch is silky, untangling is easy.

Example C 42: Oxidation dye

| | |
|---|---|
| triethanolamine laurylsulfate with 40% active material | 2.5 g |
| 2-octyl dodecanol marketed under the name of EUTANOL G by the Henkel company | 7.5 g |
| oleic diethanolamide | 7.0 g |
| oleocetyl alcohol with 30 moles of EO marketed under the name of Mergital OC 30 by the Henkel company | 3.0 g |
| oleic acid | 20 g |
| polymer of example 49 | 3 g |
| benzyl alcohol | 10 g |
| 96° ethyl alcohol | 10 g |
| ammonia at 22° Be | 16 ml |
| N,N—bis(2-hydroxyethyl) paraphenylene diamine sulfate | 1 g |
| p-aminophenol | 0.4 g |
| resorcin | 0.15 g |
| m-aminophenol | 0.10 g |
| α-naphthol | 0.40 g |
| hydroquinone | 0.10 g |

| | |
|---|---|
| -continued | |
| ethylenediaminetetraacetic acid | 0.24 g |
| sodium bisulfite (d = 1.32) | 1 ml |
| water sufficient for | 100 g |

There are mixed in a bowl 30 g of this support with 30 g of 20 volume hydrogen peroxide. A consistent gel is obtained that is pleasant to apply and adheres well to the hair.

It is applied with a brush. It is allowed to stand for 30 to 40 minutes and is rinsed. The hair is easily untangled. Touch is silky.

The hair is set and dried. The hair is glossy, lively, has body (volume), touch is silky and untangling is easy.

A DARK BLOND shade is obtained.

Example C 43: Lightening ammonia oil

| | |
|---|---|
| 2-octyl dodecanol marketed under the name of EUTANOL G by Henkel company | 8 g |
| triethanolamine lauryl sulfate at 40% active material | 3 g |
| oleic diethanol amide | 6 g |
| tallow amide hydrogenated with 50 moles of EO | 3.5 g |
| oleic acid | 18 g |
| polymer of example 51 | 2.5 g |
| 96° ethyl alcohol | 15 g |
| propylene glycol | 13 g |
| ammonia at 22° Be | 16 ml |
| ethylenediaminetetraacetic acid sold under the name Trilon B | 0.3 g |
| water sufficient for | 100 g |

There are mixed in a bowl before use 40 g of this formula with 40 g of 30 volume hydrogen peroxide.

A gel is obtained that is pleasant to apply and which adheres well to hair upon application with a brush. It is allowed to stand 30 to 45 minutes and is rinsed.

The wet hair easily untangles, touch is silky. After drying, it is glossy, lively, had body (volume), touch is silky and untangling is easy.

The hair is in a much better condition than after bleaching with the same formula but with a cationic polymer.

On a dark brown hair a DARK BLOND BLEACHING is obtained.

Example C 44: Oxidation dye

| | |
|---|---|
| cetyl stearyl alcohol | 18 g |
| 2-octyl dodecanol marketed under the name of EUTANOL G by the Henkel company | 3 g |
| stearyl alcohol oxyethylenated with 15 moles of EO | 3 g |
| ammonium lauryl sulfate (30% active material) | 12 g |
| polymer of example 52 | 3 g |
| ammonia at 22° Be | 13 ml |
| 1-amino (2-methoxyethyl)4-amino benzene dihydrochloride | 1.6 g |
| p-aminophenol | 0.3 g |
| resorcin | 0.2 g |
| m-aminophenol | 0.25 g |
| N(2-hydroxyethyl) 5-amino 2-methyl phenol | 0.02 g |
| 1-(2-hydroxy ethyloxy) 2,4-diamino benzene | 0.02 g |
| ethylenediaminetetraacetic acid sold under the name Trilon B | 0.02 g |
| sodium bisulfite d = 1.32 | 1 ml |
| water sufficient for | 100 g |

There are mixed in a bowl 30 g of this formula with 45 g of 20 volume hydrogen peroxide.

A smooth cream is obtained that is pleasant to apply and which adheres well to the hair. This cream is applied to the hair with a brush.

It is allowed to stand for 30 minutes and is rinsed. The hair easily untangles and touch is silky.

The hair is set and dried. The hair is glossy, lively and has body, touch is silky and untangling is easy.

A LIGHT BROWN shade is obtained.

Example C 45: Shampoo

| | |
|---|---|
| polymer of example 43 | 0.8 g |
| stearate of polyoxyethylene with 8 moles of EO sold under the name Mirj 45 by the Atlas Powder company | 10 g |
| nonionic surfactant with a base of lauric alcohol polyglycerolated (4.2 moles) in solution with about 60% active material | 8 g |

$$C_{12}H_{25}\text{---}\left[\text{O---CH}_2\text{---CH}\underset{\underset{\text{CH}_2\text{OH}}{|}}{\phantom{X}}\right]_n\text{---OH}$$

| | |
|---|---|
| n = statistical value of about 4.2 | |
| water sufficient for | 100 g |

The pH is adjusted to 5.1.

Example C 46: Shampoo

| | |
|---|---|
| polymer of example 44 | 0.05 g |
| aqueous solution of mixed sodium and triethanolamine salts of lipoamino acids obtained by combination of lauric acid with amino acids from total hydrolysis of collagen, with 22% active material sold under the name LIPOPROTEOL LCO by the Rhone-Poulenc company | 32 g |
| triethanolamine salt of the product of condensation of copra acid and animal protein hydrolysate with 40% active material sold under the name MAYPON 4 CT by the Stepan company | 20 g |
| hydroxypropylmethyl cellulose sold under the name METHOCEL F 4M by the Dow company | 0.2 g |
| water sufficient for | 100 g |

The pH is adjusted to 8.

Example C 47: Shampoo

| | |
|---|---|
| polymer of example 52 | 0.1 g |
| alkyl ($C_{12}$–$C_{18}$) dimethylcarboxymethylammonium hydroxide with 30% active material sold under the name DEHYTON AB 30 by the Henkel Company | 4 g |
| Na alkyl ($C_{12}$–$C_{14}$) ether sulfate (2.2 moles of EO) with 25% active material | 17 g |
| copra diethanolamide | 3 g |
| methyl paraoxybenzoate | 0.3 g |
| water sufficient for | 100 g |

The pH is adjusted to 7.1.

Example C 48: Shampoo

| | |
|---|---|
| polymer of example 49 | 0.6 g |
| triethanolamine alkyl ($C_{12}$–$C_{14}$) sulfate with 40% active material | 15 g |
| surfactant of the formula: R—(OCH$_2$—CH$_2$)$_x$ OCH$_2$COOH R being a mixture of alkyl $C_{12}$–$C_{14}$ radicals x is equal to 10, product with 90% active material sold under the name AKYPO RL M 100 by the CHEM-Y company | 2.5 g |
| copra diethanolamide | 2 g |
| ammonium chloride | 1 g |
| water sufficient for | 100 g |

The pH is adjusted to 5.4.

Example C 49: Shampoo

| | |
|---|---|
| polymer of formula 46 | 0.3 g |
| surfactant of the formula: | 7 g |
| R—CO—NH—CH$_2$—CH$_2$O—CH$_2$—CH$_2$(—O—CH$_2$—CHOH—CH$_2$)$_{3.5}$OH | |
| R = natural fatty acid amides of C$_{12}$—C$_{18}$ | |
| alkyl glycoside of the formula: | 5 g |

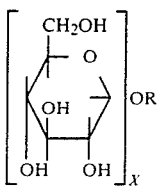

x = 1 a 5
R = C$_8$—C$_{10}$

| | |
|---|---|
| product with 70% active material sold under the name TRITON CG 110 by the Seppic company | |
| copra diethanolamide | 3.8 g |
| water sufficient for | 100 g |

The pH is adjusted to 6.2.

Example C 50: Shampoo

| | |
|---|---|
| polymer of example 51 | 1.2 g |
| cycloimidazoline derivative of coconut oil with 38% active material sold under the name MIRANOL C2M conc by the Miranol company | 10 g |

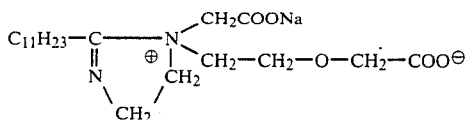

| | |
|---|---|
| tetradecyltrimethylammonium chloride | 3 g |
| potassium salt of a condensate of collagen protein and coconut fatty acid with a molecular weight of 700-800 with 30% active material sold under the name LEXEINE S 620 by the Inolex company | 2 g |
| methyl paraoxybenzoate | 0.3 g |
| water sufficient for | 100 g |

The pH is adjusted to 4.2.

Example C 51: Rinse

| | |
|---|---|
| polymer of example 43 | 1.5 g |
| mixture of cetylstearyl alcohol and cetylstearyl alcohol oxyethylenated with 15 moles of EO | 2 g |
| cetylstearyl alcohol with 15 moles of EO sold under the name CEMUSOL OR 30 by the S.P.C.S. company | 3 g |
| hydroxyethylcellulose sold under the name CELLOSIZE QP 4400 by the Union Carbide company | 0.6 g |
| bis (2-hydroxyethyl) amine coconut oxide with 39% active material sold under the name AROMOX C12/W by the AKZO company | 2.5 g |
| water sufficient for | 100 g |

The pH is adjusted to 5.9.

Example C 52: Rinse

| | |
|---|---|
| polymer of example 49 | 0.4 g |
| cetylstearyl alcohol | 2 g |
| mixture of fatty alcohols and oxyethylenated products sold under the name POLAWAX GP 200 by the Croda (Ltd) company | 3 g |
| diethylamine coconut oxide with 39% active material sold under the name AROMOX DMCD by the Akzo Chemie company | 5 g |
| chlorhexidine hydrochloride (in powder) | 0.05 g |
| water sufficient for | 100 g |

The pH is adjusted to 6.4.

Example C 53: Rinse

| | |
|---|---|
| polymer of example 51 | 0.9 g |
| mixture of cetylstearyl alcohol and cetylstearyl alcohol oxyethylenated with 15 moles of EO | 2 g |
| cetylstearyl alcohol with 15 moles EO sold under the name CEMUSOL OR 30 by the S.P.C.S. company | 3 g |
| hydroxyethylcellulose sold under the name CELLOSIZE QP 4400 by the Union Carbide company | 0.7 g |
| tetradecyltrimethylammonium chloride | 2 g |
| chlorhexidine hydrochloride | 0.05 g |
| water sufficient for | 100 g |

The pH is adjusted to 6.9.

Example C 54: Hair care cream

| | |
|---|---|
| cetylstearyl alcohol | 25 g |
| stearyl alcohol | 5 g |
| sodium cetylstearyl sulfate | 5 g |
| polymer of example 21 | 2 g |
| water sufficient for | 100 g |

This cream is applied to clean, wet and wiped hair in sufficient amount (60–80 g) to impregnate and cover the hair well.
It is allowed to stand 15 to 25 minutes and rinsed.
The wet hair is very soft and easy to untangle. It is set and dried under a drier.
The dried hair easily untangles and has a silky touch; it is glossy, lively and has body and volume.

Example C 55: Oxidation dye

| | |
|---|---|
| cetylstearyl alcohol | 18 g |
| 2-octyl dodecanol sold under the name EUTANOL G by the Henkel company | 3 g |
| stearyl alcohol oxyethylenated (15) | 3 g |
| ammonium lauryl sulfate (30% active material) | 12 g |
| polymer of example 26 | 3 g |

-continued

| | |
|---|---|
| ammonia at 22° Be | 13 ml |
| 1-amino (2-methoxyethyl) 4-amino benzene dihydrochloride | 1.6 g |
| p-aminophenol | 0.3 g |
| resorcin | 0.2 g |
| m-aminophenol | 0.25 g |
| N(2-hydroxyethyl) 5-amino 2-methyl phenol | 0.02 g |
| 1-(2-hydroxyethyloxy) 2,4-diamino benzene dihydrochloride | 0.02 g |
| ethylenediaminetetraacetic acid sold under the name TRILON B | 0.02 g |
| sodium bisulfite d = 1.32 | 1 ml |
| water sufficient for | 100 g |

There are mixed in a bowl 30 g of this formula with 45 g of 20 volume hydrogen peroxide.

A smooth cream is obtained that is pleasant to apply and adheres well to the hair.

This cream is applied to the hair with a brush.

It is allowed to stand for 30 minutes and rinsed.

The hair easily untangles and the touch is silky. The hair is set and dried.

The hair is glossy, lively and has volume, touch is silky and untangling is easy.

A LIGHT BROWN shade is obtained.

We claim:

1. A hair dye composition comprising an aqueous solution of a quaternized polymer containing units of the formula

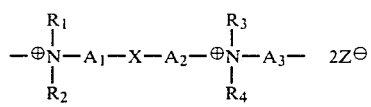

$R_1$, $R_2$, $R_3$ and $R_4$ each independently represent a hydrocarbon group, or at least one of the pairs $R_1$, $R_2$ and $R_3$, $R_4$ represents together with the nitrogen atom to which it is attached a heterocycle optionally containing an oxygen or sulfur heteroatom;

$A_1$ and $A_2$, each independently, represent linear or branched alkylene or arylene, substituted or not, containing up to 20 carbon atoms;

X represents a bivalent group of the formula (a) 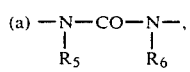

(b) 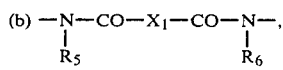

(c) 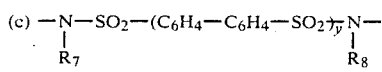

(d) 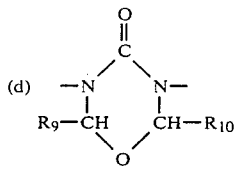

(e) —CO—NH—,
(f) —CO—O—,
(g) —O—CO—NH—,
(h) —CO—$X_2$—CO—,
(i) —CO—$X'_2$—CO—, or
(j) —O—CO—$X_3$—CO—O—, wherein y is equal to 0 or 1, $R_5$, $R_6$, $R_7$, $R_8$, $R_9$ and $R_{10}$ represent hydrogen or lower alkyl, $X_1$ represents alkylene, alkylene including an —S—S— group, alkenylene, arylene, diaminoalkylene, diaminoarylene, dioxyalkylene, dioxyarylene or polyoxyalkylene, or $X_1$ represents a direct covalent bond, $X_2$ represents diaminoalkylene, dioxyalkylene or polyoxyalkylene bivalent group, $X'_2$ represents dithioalkylene, $X_3$ represents alkylene, cycloalkylene, arylene, diaminoalkylene, diaminocycloalkylene or diaminoarylene, $A_3$ represents —$B_1$—Y—$B_2$, wherein $B_1$ and $B_2$ represent alkylene or arylene and Y has the same meaning as X above, or Y represents

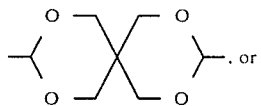

$A_3$ represents —$B_3$—$Y_1$—$B_4$, wherein $B_3$ and $B_4$ represent arylene and $Y_1$ represents linear or branched alkylene, or linear or branched alkylene substituted by at least one —OH or =O group, or $Y_1$ represents a heteroatom selected from oxygen, sulfur or nitrogen, or $A_3$ represents (a) —E—(—O—D)$_{z'}$—O—E— or
(b) —E—O—G—O—E—, wherein $z'$ is a number ranging from 2 to 600, E represents alkylene having 1-4 carbon atoms or —$CH_2$—CHOH—$CH_2$—, D represents a bivalent hydrocarbon group containing 1-5 carbon atoms, and G represents alkylene, cycloalkylene, arylene or aralkylene, or when X is other than —CO—$X_2$—CO—, $A_3$ represents linear or branched alkylene or hydroxyalkylene, alkenylene or hydroxyalkenylene, cycloalkylene, or cycloalkenylene, containing up to 20 carbon atoms;

and $Z^\ominus$ represents a halide anion;

with the proviso that when X represents —NH—CO—NH—, $A_3$ represents —E—(O—D)$_{z'}$—O—E— or —$B_1$—Y—$B_2$, wherein Y has the meaning given for X above except for the value —NH—CO—NH—, or $A_3$ represents —E—O—G—O—E— wherein E and G have the meanings given above with the proviso that E and G are not simultaneously alkylene;

and a hair dyeing amount of a hair dye.

2. The hair dye composition of claim 1 wherein said hair dye is present in an amount from 0.5 to 15 percent by weight of said composition.

3. The hair dye composition of claim 1 which also includes a soap or fatty alcohol and an emulsifier.

4. The hair dye composition of claim 2 which also includes an alkalizing agent in an amount such that the pH of the composition is between 8 and 11.

5. The hair dye composition of claim 4 wherein said alkalizing agent is ammonia, monoethanolamine, diethanolamine or triethanolamine.

6. The hair dye composition of claim 1 wherein said hair dye is an oxidation dye.

7. The hair dye composition of claim 6 which also includes an effective hair dyeing amount of a direct hair dye.

8. A hair dye composition packaged into two parts, said first part comprising an aqueous solution of a quaternized polymer containing units of the formula

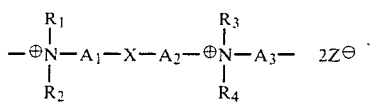

wherein

- $R_1$, $R_2$, $R_3$ and $R_4$ each independently represent a hydrocarbon group, or at least one of the pairs $R_1$, $R_2$ and $R_3$, $R_4$ represents together with the nitrogen atom to which it is attached a heterocycle optionally containing an oxygen or sulfur heteroatom;
- $A_1$ and $A_2$, each independently, represent linear or branched alkylene or arylene, substituted or not, containing up to 20 carbon atoms;
- X represents a bivalent group of the formula

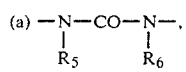

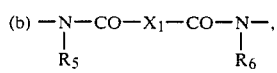

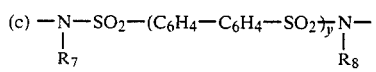

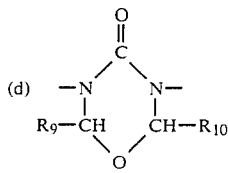

(e) —CO—NH—,
(f) —CO—O—,
(g) —O—CO—NH—,
(h) —CO—$X_2$—CO—,
(i) —CO—$X'_2$—CO—, or
(j) —O—CO—$X_3$—CO—O—, wherein
y is equal to 0 or 1,
$R_5$, $R_6$, $R_7$, $R_8$, $R_9$ and $R_{10}$ represent hydrogen or lower alkyl,
$X_1$ represents alkylene, alkylene including an —S—S— group, alkenylene, arylene, diaminoalkylene, diaminoarylene, dioxyalkylene, dioxyarylene or polyoxyalkylene, or $X_1$ represents a direct covalent bond,
$X_2$ represents diaminoalkylene, dioxyalkylene or polyoxyalkylene bivalent group,
$X'_2$ represents dithioalkylene,
$X_3$ represents alkylene, cycloalkylene, arylene, diaminoalkylene, diaminocycloalkylene or diaminoarylene, $A_3$ represents —$B_1$—Y—$B_2$, wherein $B_1$ and $B_2$ represent alkylene or arylene and Y has the same meaning as X above, or Y represents

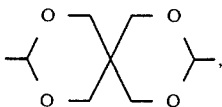

or $A_3$ represents —$B_3$—$Y_1$—$B_4$, wherein $B_3$ and $B_4$ represent arylene and $Y_1$ represents linear or branched alkylene, or linear or branched alkylene substituted by at least one —OH or =O group, or $Y_1$ represents a heteroatom selected from oxygen, sulfur or nitrogen, or $A_3$ represents (a) —E—O—D)O—E— or
(b) —E—O—G—O—E—, wherein
z is a number ranging from 2 to 600,
E represents alkylene having 1-4 carbon atoms or —$CH_2$—CHOH—$CH_2$—,
D represents a bivalent hydrocarbon group containing 1-5 carbon atoms, and
G represents alkylene, cycloalkylene, arylene or aralkylene, or when X is other than —CO—$X_2$—CO—, $A_3$ represents linear or branched alkylene or hydroxyalkylene, alkenylene or hydroxyalkenylene, cycloalkylene, or cycloalkenylene, containing up to 20 carbon atoms;

and $Z^\ominus$ represents a halide anion;

with the proviso that when X represents —NH—CO—NH—, $A_3$ represents —E—(O—D)$_z$—O—E— or —$B_1$—Y—$B_2$, wherein Y has the meaning given for X above except for the value —NH—CO—NH—, or $A_3$ represents —E—O—G—O—E— wherein E and G have the meanings given above with the proviso that E and G are not simultaneously alkylene; and a hair dyeing amount of an oxidation hair dye;

and said second part comprising hydrogen peroxide, said two parts being mixed at the time of use.

9. The hair dye composition of claim 8 wherein said polymer is present in an amount of 0.5 to 15 percent by weight of said composition.

10. A two-part hair bleaching composition comprising, as said first part, an aqueous solution of a quaternized polymer containing units of the formula

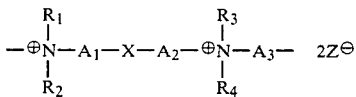

wherein $R_1$, $R_2$, $R_3$ and $R_4$ each independently represent a hydrocarbon group, or at least one of the pairs $R_1$, $R_2$ and $R_3$, $R_4$ represents together with the nitrogen atom to which it is attached a heterocycle optionally containing an oxygen or sulfur heteroatom;

$A_1$ and $A_2$, each independently, represent linear or branched alkylene or arylene, substituted or not, containing up to 20 carbon atoms;

X represents a bivalent group of the formula (a) 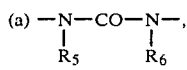

(b) 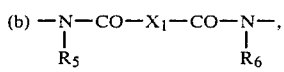

(c) 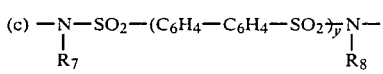

(d) 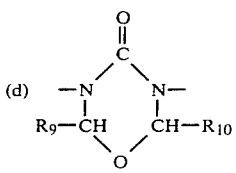

(e) —CO—NH—,
(f) —CO—O—,
(g) —O—CO—NH—,
(h) —CO—$X_2$—CO—,
(i) —CO—$X'_2$—CO—, or
(j) —O—CO—$X_3$—CO—O—, wherein
y is equal to 0 or 1, $R_5$, $R_6$, $R_7$, $R_8$, $R_9$ and $R_{10}$ represent hydrogen or lower alkyl, $X_1$ represents alkylene, alkylene including an —S—S— group, alkenylene, arylene, diaminoalkylene, diaminoarylene, dioxyalkylene, dioxyarylene or polyoxyalkylene, or $X_1$ represents a direct covalent bond, $X_2$ represents diaminoalkylene, dioxyalkylene or polyoxyalkylene bivalent group, $X'_2$ represents dithioalkylene, $X_3$ represents alkylene, cycloalkylene, arylene, diaminoalkylene, diaminocycloalkylene or diaminoarylene, $A_3$ represents —$B_1$—Y—$B_2$, wherein $B_1$ and $B_2$ represent alkylene or arylene and Y has the same meaning as X above, or Y represents

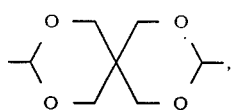

or $A_3$ represents —$B_3$—$Y_1$—$B_4$, wherein $B_3$ and $B_4$ represent arylene and $Y_1$ represents linear or branched alkylene, or linear or branched alkylene substituted by at least one —OH or =O group, or $Y_1$ represents a heteroatom selected from oxygen, sulfur or nitrogen, or $A_3$ represents
(a) —E—(O—D)$_z$—O—E— or
(b) —E—O—G—O—E—, wherein z is a number ranging from 2 to 600, E represents alkylene having 1-4 carbon atoms or —$CH_2$—CHOH—$CH_2$—, D represents a bivalent hydrocarbon group containing 1-5 carbon atoms, and G represents alkylene, cycloalkylene, arylene or aralkylene, or when X is other than —CO—$X_2$—CO—, $A_3$ represents linear or branched alkylene or hydroxyalkylene, alkenylene or hydroxyalkenylene, cycloalkylene, or cycloalkenylene, containing up to 20 carbon atoms;

and $Z^\ominus$ represents a halide anion;

with the proviso that when X represents —NH—CO—NH—, $A_3$ represents —E—(O—D)$_z$—O—E— or —$B_1$—Y—$B_2$, wherein Y has the meaning given for X above except for the value —NH—CO—NH—, or $A_3$ represents —E—O—G—O—E— wherein E and G have the meanings given above with the proviso that E and G are not simultaneously alkylene;

and said second part comprises a hair bleaching amount of hydrogen peroxide or a solution of a persulfate, a perborate or a percarbonate.

11. A hair dye composition comprising an aqueous solution of a quaternized polymer containing units of the formula

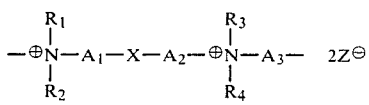

wherein $R_1$, $R_2$, $R_3$ and $R_4$ each independently represent a hydrocarbon group, or at least one of the pairs $R_1$, $R_2$ and $R_3$, $R_4$ represent together with the nitrogen atom to which it is attached a heterocycle optionally containing an oxygen or sulfur heteroatom;

$A_1$ and $A_2$, each independently, represent linear or branched alkylene or arylene, substituted or not, containing up to 20 carbon atoms;

X represents a bivalent group of the formula (a) 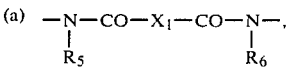

(b) 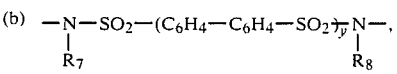

(c) 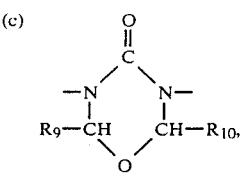

(d) —CO—NH—,
(e) —CO—O—,
(f) —O—CO—NH—,
(g) —CO—$X_2$—CO—,
(h) —CO—$X'_2$—CO—, or
(i) —O—CO—$X_3$—CO—O—, wherein
y is equal to 0 to 1, $R_5$, $R_6$, $R_7$, $R_8$, $R_9$ and $R_{10}$ represent hydrogen or lower alkyl, $X_1$ represents alkylene, alkylene including an —S—S—group, alkenylene, arylene, diaminoalkylene, diaminoarylene, dioxyalkylene, dioxyarylene or polyoxyalkylene, or $X_1$ represents a direct covalent bond, X₂ represents diaminoalkylene, dioxyalkylene or polyoxyalkylene bivalent group, X′₂ represents dithioalkylene, X₃ represents alkylene, cycloalkylene, arylene, diaminoalkylene, diaminocycloalkylene or diaminoarylene, A₃ represents —B₁—Y—B₂, wherein B₁ and B₂ represent alkylene or arylene and Y has the same meaning as X above, or Y represents

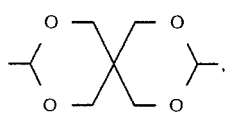

or

A₃ represents —B₃—Y₁—B₄, wherein B₃ and B₄ represent arylene and Y₁ represents linear or branched alkylene, or linear or branched alkylene substituted by at least one —OH or =O group, or Y₁ represents a heteroatom selected from oxygen, sulfur or nitrogen, or A₃ represents (a) —E—(O—D)$_{z'}$—O—E— or (b) —E—O—G—O—E—, wherein z′ is a number ranging from 2 to 600, E represents alkylene having 1-4 carbon atoms or —CH₂—CHOH—CH₂—, D represents a bivalent hydrocarbon group containing 1-5 carbon atoms, and G represents alkylene, cycloalkylene, arylene or aralkylene, or when X is other than —CO—X₂—CO—, A₃ represents linear or branched alkylene or hydroxyalkylene, alkenylene or hydroxyalkenylene, cycloalkylene, or cycloalkenylene, containing up to 20 carbon atoms;

and Z⊖ represents a halide anion; and a hair dyeing amount of a hair dye.

12. A hair dye composition packaged into two parts, said first part comprising an aqueous solution of a quaternized polymer containing units of the formula

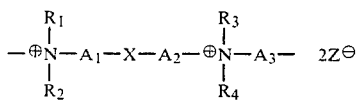

wherein

R₁, R₂, R₃ and R₄ each independently represent a hydrocarbon group, or at least one of the pairs R₁, R₂ and R₃, R₄ represents together with the nitrogen atom to which it is attached a heterocycle optionally containing an oxygen or sulfur heteroatom;

A₁ and A₂, each independently, represent linear or branched alkylene or arylene, substituted or not, containing up to 20 carbon atoms;

X represents a bivalent group of the formula (a) 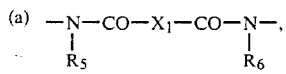

(b) 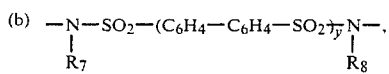

(c) 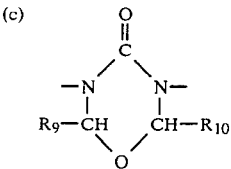

(d) —CO—NH—,
(e) —CO—O—,
(f) —O—CO—NH—,
(g) —CO—X₂—CO—,
(h) —CO—X′₂—CO—, or
(i) —O—CO—X₃—CO—O—, wherein y is equal to 0 or 1, R₅, R₆, R₇, R₈, R₉ and R₁₀ represent hydrogen or lower alkyl, X₁ represents alkylene, alkylene including an —S—S— group, alkenylene, arylene, diaminoalkylene, diaminoarylene, dioxyalkylene, dioxyarylene or polyoxyalkylene, or X₁ represents a direct covalent bond, X₂ represents diaminoalkylene, dioxyalkylene or polyoxyalkylene bivalent group, X′₂ represents dithioalkylene, X₃ represents alkylene, cycloalkylene, arylene, diaminoalkylene, diaminocycloalkylene or diaminoarylene, A₃ represents —B₁—Y—B₂, wherein B₁ and B₂ represent alkylene or arylene and Y has the same meaning as X above, or Y represents

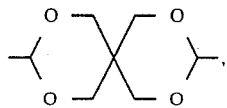

or

A₃ represents —B₃—Y₁—B₄, wherein B₃ and B₄ represent arylene and Y₁ represents linear or branched alkylene, or linear or branched alkylene substituted by at least one —OH or =O group, or Y₁ represents a heteroatom selected from oxygen, sulfur or nitrogen, or A₃ represents (a) —E—(O—D)$_{z'}$—O—E— or (b) —E—O—G—O—E—, wherein z′ is a number ranging from 2 to 600, E represents alkylene having 1-4 carbon atoms or —CH₂—CHOH—CH₂—, D represents a bivalent hydrocarbon group containing 1-5 carbon atoms, and G represents alkylene, cycloalkylene, arylene or aralkylene, or when X is other than —CO—X₂—CO—, A₃ represents linear or branched alkylene or hydroxyalkylene, alkenylene or hydroxyalkenylene, cycloalkylene, or cycloalkenylene, containing up to 20 carbon atoms;

and Z⊖ represents a halide anion; and a hair dyeing amount of an oxidation hair dye; and said second part comprising hydrogen peroxide, said two parts being mixed at the time of use.

13. A two-part hair bleaching composition comprising, as said first part, an aqueous solution of a quaternized polymer containing units of the formula

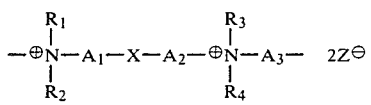

wherein
- $R_1$, $R_2$, $R_3$ and $R_4$ each independently represent a hydrocarbon group, or at least one of the pairs $R_1$, $R_2$ and $R_3$, $R_4$ represents together with the nitrogen atom to which it is attached a heterocycle optionally containing an oxygen or sulfur heteroatom;
- $A_1$ and $A_2$, each independently, represent linear or branched alkylene or arylene, substituted or not, containing up to 20 carbon atoms;
- X represents a bivalent group of the formula (a) 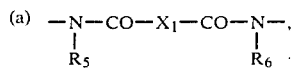

(b) 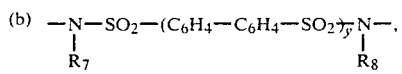

(c) 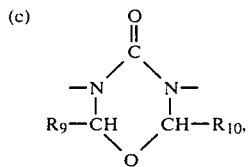

(d) —CO—NH—,
(e) —CO—O—,
(f) —O—CO—NH—,
(g) —CO—$X_2$—CO—,
(h) —CO—$X'_2$—CO—, or
(i) —O—CO—$X_3$—CO—O—, wherein
- y is equal to 0 to 1,
- $R_5$, $R_6$, $R_7$, $R_8$, $R_9$ and $R_{10}$ represent hydrogen or lower alkyl,
- $X_1$ represents alkylene, alkylene including an —S—S— group, alkenylene, arylene, diaminoalkylene, diaminoarylene, dioxyalkylene, dioxyarylene or polyoxyalkylene, or $X_1$ represents a direct covalent bond,
- $X_2$ represents diaminoalkylene, dioxyalkylene or polyoxyalkylene bivalent group,
- $X'_2$ represents dithioalkylene,
- $X_3$ represents alkylene, cycloalkylene, arylene, diaminoalkylene, diaminocycloalkylene or diaminoarylene,
- $A_3$ represents —$B_1$—Y—$B_2$, wherein $B_1$ and $B_2$ represent alkylene or arylene and Y has the same meaning as X above, or
- Y represents

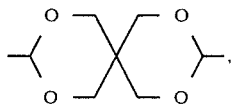

or
- $A_3$ represents —$B_3$—$Y_1$—$B_4$, wherein $B_3$ and $B_4$ represent arylene and $Y_1$ represents linear or branched alkylene, or linear or branched alkylene substituted by at least one —OH or =O group, or $Y_1$ represents a heteroatom selected from oxygen, sulfur or nitrogen, or
- $A_3$ represents
  (a) —E—(O—D)$_{z'}$—O—E— or
  (b) —E—O—G—O—E—, wherein $z'$ is a number ranging from 2 to 600,
- E represents alkylene having 1-4 carbon atoms or —$CH_2$—CHOH—$CH_2$—,
- D represents a bivalent hydrocarbon group containing 1-5 carbon atoms, and
- G represents alkylene, cycloalkylene, arylene or aralkylene, or
- when X is other than —CO—$X_2$—CO—, $A_3$ represents linear or branched alkylene or hydroxyalkylene, alkenylene or hydroxyalkenylene, cycloalkylene, or cycloalkenylene, containing up to 20 carbon atoms;
- and $Z^\ominus$ represents a halide anion;
- and said second part comprises a hair bleaching amount of hydrogen peroxide or a solution of a persulfate, a perborate or a percarbonate.

* * * * *

UNITED STATES PATENT AND TRADEMARK OFFICE
CERTIFICATE OF CORRECTION

PATENT NO. : 4,517,174
DATED : May 14, 1985
INVENTOR(S) : Jacquet et al

It is certified that error appears in the above-identified patent and that said Letters Patent is hereby corrected as shown below:

Col. 45, line 17, after "or" insert the following:

--$A_3$ is a linear or branched alkylene substituted by one or more -OH or =O groups, or--.

Signed and Sealed this

Third Day of December, 1991

Attest:

HARRY F. MANBECK, JR.

*Attesting Officer*   Commissioner of Patents and Trademarks